US005861124A

United States Patent [19]
Hosoi et al.

[11] Patent Number: 5,861,124
[45] Date of Patent: *Jan. 19, 1999

[54] METHOD AND APPARATUS FOR DETECTING DENATURATION OF NUCLEIC ACID

[75] Inventors: Shigeru Hosoi; Tadashi Fukami; Akihiko Tsuji; Makiko Hiyoshi, all of Hamamatsu, Japan

[73] Assignee: Hamamatsu Photonics KK, Shizuoka-ken, Japan

[*] Notice: The term of this patent shall not extend beyond the expiration date of Pat. No. 5,599,504.

[21] Appl. No.: 296,893

[22] Filed: Aug. 29, 1994

Related U.S. Application Data

[63] Continuation-in-part of Ser. No. 275,910, Jul. 15, 1994, Pat. No. 5,599,504.

[30] Foreign Application Priority Data

Jul. 15, 1993 [JP] Japan ................................... 5-175730

[51] Int. Cl.$^6$ .................................................. G01N 21/64
[52] U.S. Cl. ........................ 422/82.08; 422/68.1; 422/50; 422/52; 422/55; 422/57; 422/82.09; 435/6; 435/91.2; 435/287.2; 435/283.1; 435/288.1; 435/289.1; 435/290.1; 435/290.4; 356/344; 73/61.58; 204/452
[58] Field of Search .............................. 422/80.08, 68.1, 422/50, 52, 55, 57, 82.09; 436/55, 94, 147; 435/6, 91.1, 91.2, 174, 287.2, 288.7, 181, 239, 820, 283.1, 287.1, 288.1, 288.2, 289.1, 290.1, 290.4; 356/344; 73/61.58; 204/452

[56] References Cited

U.S. PATENT DOCUMENTS

| | | | |
|---|---|---|---|
| 4,822,733 | 4/1989 | Morrison et al. | 435/6 |
| 4,822,746 | 4/1989 | Walt . | |
| 4,855,930 | 8/1989 | Chao et al. | 364/497 |
| 5,348,853 | 9/1994 | Wang et al. | 435/6 |
| 5,599,504 | 2/1997 | Hosoi et al. | 422/82.08 |

FOREIGN PATENT DOCUMENTS

| | | |
|---|---|---|
| 0070685 | 1/1983 | European Pat. Off. . |
| 0229943 | 7/1987 | European Pat. Off. . |
| 0232967 | 8/1987 | European Pat. Off. . |
| 9200388 | 1/1992 | WIPO . |

OTHER PUBLICATIONS

Fischer et al, "DNA Fragments Differing by Single Base–Pair Substitutions are Separated in Denaturing Gradient Gels: Correspondence With Melting Theory", Proc. Natl. Acad. Sci. USA, vol. 80, pp. 1579–1583, Mar. 1983.

Woolford et al, "Simplified Procedures for Detection of Amplified DNA Using Fluorescent Label Incorporation and Reverse Probing", FEMS Microbiology Letters 99 (1992) pp. 311–316.

Kobayashi et al, "Novel DNA Sequence Detection Method Based on Fluorescence Energy Transfer", pp. 370–377 vol. # not applicable.

Morrison, "Detection of Energy Transfer and Fluorescence Quenching", Nonisotopic DNA Probe Techniques, pp. 311–352.

(List continued on next page.)

*Primary Examiner*—W. Gary Jones
*Assistant Examiner*—Dianne Rees
*Attorney, Agent, or Firm*—Cushman Darby & Cushman IP Group of Pillsbury Madison & Sutro LLP

[57] ABSTRACT

An apparatus for detecting denaturation of a nucleic acid, including: denaturation condition controlling means for controlling condition of denaturation under which a double-stranded nucleic acid is separated into a first single-stranded nucleic acid and a second single-stranded nucleic acid; excitation light irradiation means for irradiating the double-stranded nucleic acid before denaturation, and the first single-stranded nucleic acid and second single-stranded nucleic acid after the denaturation; fluorescence detection means for detecting fluorescence emission based on the excitation light irradiation; and processing means for receiving, storing and processing a signal supplied from the fluorescence detection means.

12 Claims, 17 Drawing Sheets

OTHER PUBLICATIONS

Analytical Biochemistry 221, 00–00 (1994) Assay of DNA Denaturation by Polymerase Chain Reaction–Driven Fluorescent Label Incorporation and Fluorescence Resonance Energy Transfer, Makiko Hiyoshi et al pp. 1–6.

Morrison et al, "Solution–Phase Detection of Polynucleotides Using Interacting Fluorescent Labels and Competitive Hybridization", Analytical Biochemistry, 183:231–244 (1989).

Morrison and Stol, Biochemistry 32:3095–3104, 1993 Sensitive Fluorescence–Based Thermodynamic and Kinetic Measurements of DNA Hybridization in Solution.

Molecular Cloning, A Lab Manual, Moniatis et al, CSH-S–pp. 86–87, 1989.

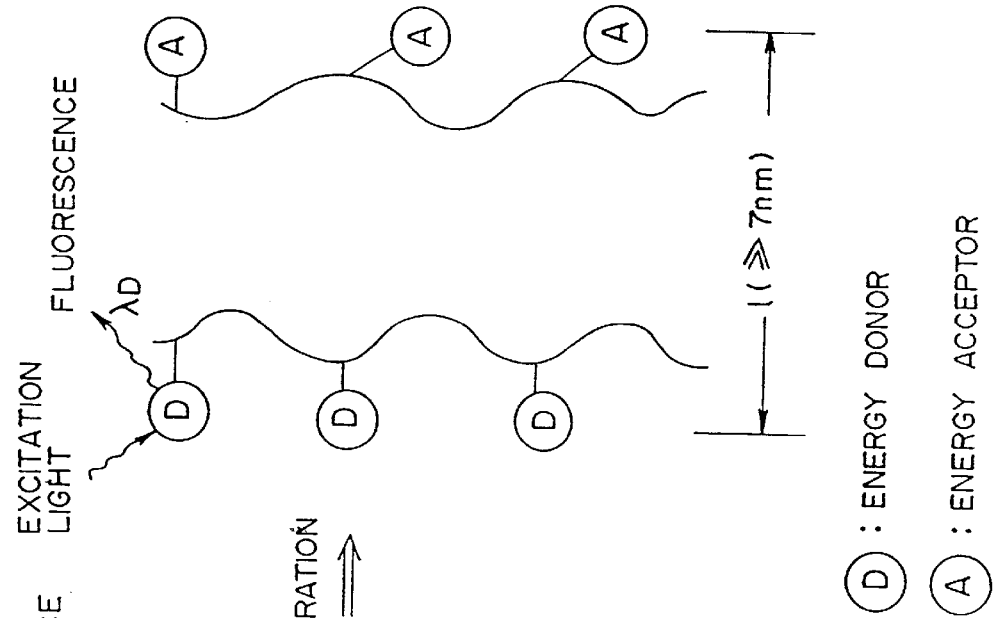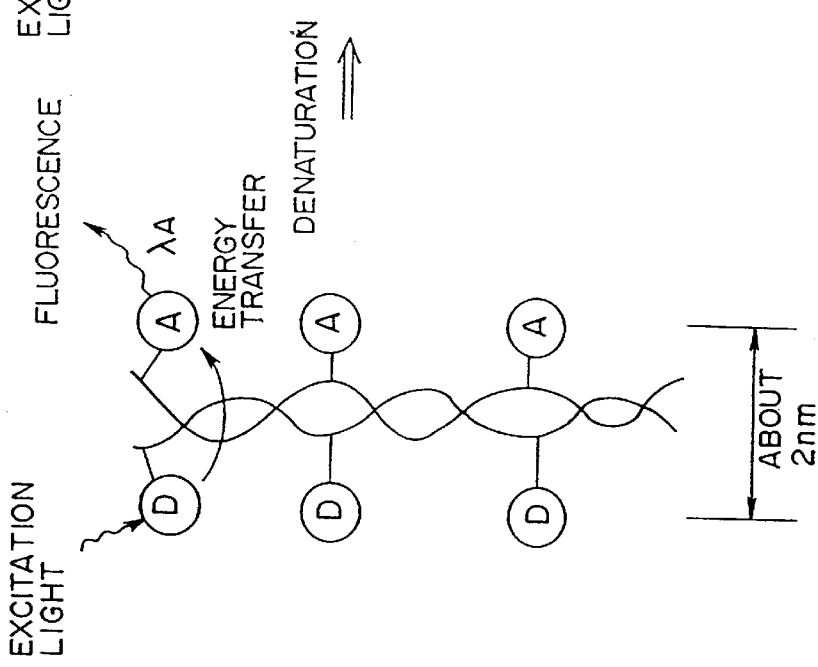

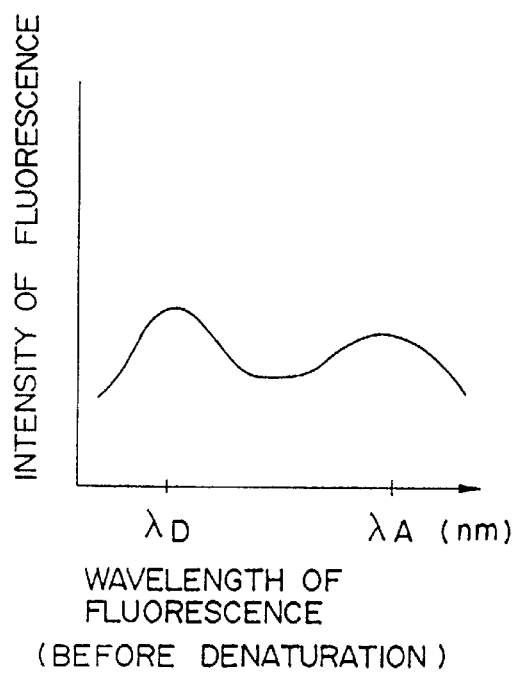
Fig. 1B1
WAVELENGTH OF FLUORESCENCE
(BEFORE DENATURATION)
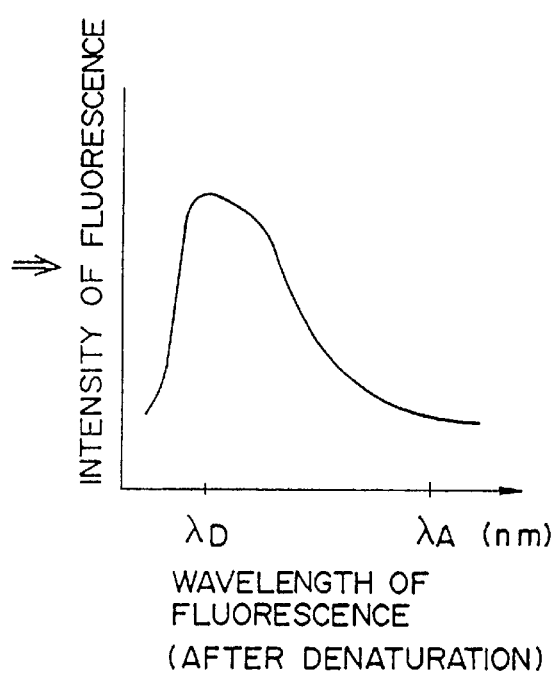
Fig. 1B2
WAVELENGTH OF FLUORESCENCE
(AFTER DENATURATION)

REFERENCE
NUCLEIC ACID

NUCLEIC ACID
TO BE EXAMINED

Fig. 7A

①②: PRIMER
Ⓑ : BIOTIN

⇓ PCR-AMPLIFICATION
IN THE PRESENCE OF
FLUORESCEIN-dUTP

⇓ PCT-AMPLIFICATION
IN THE PRESENCE OF
RHODAMINE-dUTP

Fig. 7B

Ⓓ: ENERGY DONOR (FLUORESCEIN)
Ⓐ: ENERGY ACCEPTOR (RHODAMINE)

⇓ ABSORPTION TO
SURFACE OF
AVIDIN-FIXING
MATRIX

⇓ ABSORPTION TO
SURFACE OF
AVIDIN-FIXING
MATRIX

Fig. 7C (AV): AVIDIN

THE SAME AS FIG.7(c)

⇩ ELUTION            ⇩ ELUTION

DOUBLE-STRAND FORMATION

DOUBLE-STRAND NUCLEIC ACID TO BE MEASURED

Fig. 9A1 Fig. 9A2 Fig. 9A3
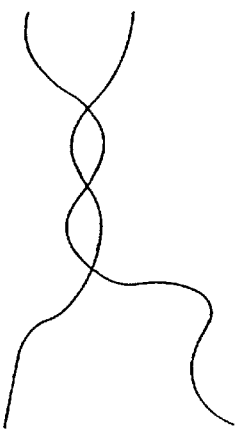
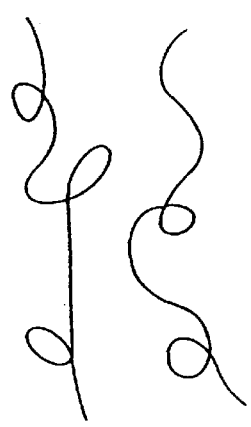
BEFORE DENATURATION (DOUBLE-STRAND) | DURING DENATURATION (PARTIALLY DOUBLE-STRAND) | AFTER DENATURATION
Fig. 9B
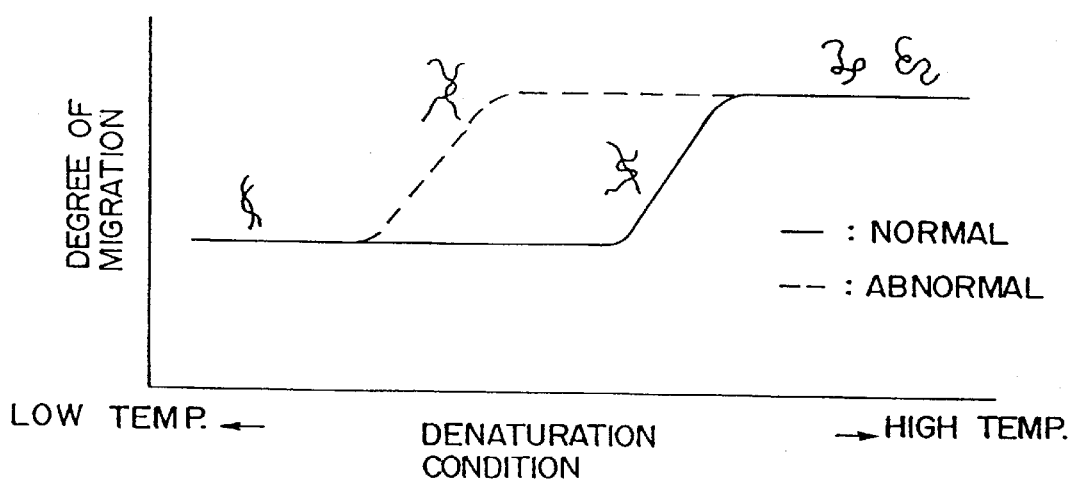
— : NORMAL
-- : ABNORMAL
LOW TEMP. ← DENATURATION CONDITION → HIGH TEMP.

METHOD AND APPARATUS FOR DETECTING DENATURATION OF NUCLEIC ACID

RELATED APPLICATION

This is a continuation-in-part application of application Ser. No. 08/275,910 filed on Jul. 15, 1994 now U.S. Pat. No. 5,599,504. for APPARATUS FOR DETECTING DENATURATION OF NUCLEIC ACID.

BACKGROUND OF THE INVENTION

1. Field of the Invention

The present invention relates to structural analysis of nucleic acids, and more particularly to an apparatus and a method for detecting denaturation of nucleic acids.

2. Related Background Art

Much attention has been given to techniques for detecting and measuring denaturation of nucleic acids (DNA, RNA, and hybrids thereof) with accuracy which substantially resolves a difference in the denaturation conditions based on a single base (or single base-pair) substitution, deletion or addition.

For the detection of slight differences between homologous double-stranded nucleic acids, such as the above-mentioned single base alteration, there has been proposed a method called "denaturing gradient gel electrophoresis method" (S. G. Fischer and L. S. Lerman: Proc. Natl. Acid. Sci. USA, Vol.80, pp.1579–1583, March 1983). In this method, a double-stranded nucleic acid to be measured is first amplified using an ordinary technique such as polymerase chain reaction (hereinafter, referred to as "PCR method"). Then, the resultant double-stranded nucleic acid is charged into a gel carrier (or gel support), and the double-stranded nucleic acid is subjected to electrophoresis under a gradient of a denaturation condition (such as temperature or hydrogen ion concentration (pH)) which is spatially provided across the gel carrier. In this measurement, it is possible to simultaneously subject a control double-stranded nucleic acid functioning as a reference (or standard) together with the double-stranded nucleic acid to be measured so as to observe a difference in the denaturation condition between these two species of the double-stranded nucleic acids (i.e., the double-stranded nucleic acid to be measured and the reference double-stranded nucleic acid).

FIGS. 9A1–9A3 and 9B are schematic diagrams illustrating the above-mentioned conventional method for detecting the denaturation of a nucleic acid. For example, FIGS. 9A1–9A3 relate to a case wherein temperature is selected as a denaturation condition, and schematically shows a state wherein a nucleic acid is denatured on the basis of temperature increase. In general, a double-stranded nucleic acid is denatured when the ambient temperature is elevated to a predetermined value. The temperature at which a double-stranded nucleic acid is denatured (denaturation temperature) depends on the composition of bases constituting the double-stranded nucleic acid. A double-stranded nucleic acid comprising a specific single-stranded nucleic acid and another single-stranded nucleic acid binding thereto which is completely complementary to the former single-stranded nucleic acid, has a denaturation temperature higher than that of a double-stranded nucleic acid comprising the above-mentioned specific single-stranded nucleic acid and another single-stranded nucleic acid binding thereto which is substantially (and not completely) complementary to the former single-stranded nucleic acid.

Conventional apparatuses for detecting denaturation of a nucleic acid utilize such a phenomenon, and conduct gel electrophoresis while spatially providing a gradient of a denaturation condition in the gel carrier to be used for the electrophoresis.

FIG. 9B shows results of measurement relating to a case of a double-stranded nucleic acid sample comprising a specific stranded and another stranded which is substantially complementary to the specific stranded. As shown in FIG. 9B, when two denaturation points (i.e., points at which denaturation occurs) are present, one double-stranded nucleic acid showing a denaturation condition of a lower temperature is the double-stranded nucleic acid to be measured, and the other double-stranded nucleic acid showing a higher temperature denaturation is the reference double-stranded nucleic acid.

However, in the above-mentioned denaturation detection of a nucleic acid utilizing the conventional denaturing gradient gel electrophoresis method, it is necessary to subject the sample nucleic acid to electrophoresis in a gel, across which a gradient or change in denaturation condition (temperature or pH) is provided. Accordingly, such a conventional denaturation detection method is troublesome or tedious. More specifically, the conventional method consumes a long period of time corresponding to several tens of minutes to several hours, while such a period of time depends on the molecular weight of the sample nucleic acid.

In addition, the sensitivity of detection of the nucleic acid denaturation by the conventional denaturing gradient gel electrophoresis method depends on the stability of the system to be used for such a purpose, the accuracy in the control of the denaturation condition such as degree of gradient to be provided to the gel, or the accuracy in the control of the condition for electrophoresis. However, it is difficult to improve the accuracy in the control of these conditions as compared with those accomplished at the present stage. Accordingly, there has been posed a problem such that further improvement is difficult with respect to the sensitivity and accuracy (or precision) of the denaturation detection.

SUMMARY OF THE INVENTION

An object of the present invention is to provide an apparatus and a method for detecting the denaturation of a nucleic acid which has solved the above-mentioned problems encountered in the conventional apparatus or method.

Another object of the present invention is to provide an apparatus and a method for detecting the denaturation of a nucleic acid which is capable of rapidly detecting the denaturation of a nucleic acid with high accuracy.

According to the present invention, there is provided an apparatus for detecting denaturation of a nucleic acid, comprising:

denaturation condition controlling means for controlling a condition of denaturation under which a double-stranded nucleic acid is separated into a first single-stranded nucleic acid and a second single-stranded nucleic acid, the first single-stranded nucleic acid comprises a base provided with a first label molecule, the second single-stranded nucleic acid having a base sequence complementary to or substantially complementary to the first single-stranded nucleic acid and comprising a base provided with a second label molecule which is capable of causing energy transfer between itself and the first label molecule located within a predetermined distance, the double-stranded nucleic acid comprising the first single-stranded nucleic acid and the second single-stranded nucleic acid binding to the first single-stranded nucleic acid;

excitation light irradiation means for emitting excitation light having a predetermined wavelength to irradiate the double-stranded nucleic acid before denaturation, and the first single-stranded nucleic acid and second single-stranded nucleic acid after the denaturation, with the excitation light;

fluorescence detection means for detecting fluorescence emission which is based on the excitation light irradiation and is capable of being changed depending on a change in the amount of energy transfer between the first label molecule and the second label molecule; and processing means for receiving, storing and processing a signal supplied from the fluorescence detection means;

whereby the fluorescence emitted from the nucleic acid is observed while changing the denaturation condition by the denaturation condition controlling means, and a denaturation point (denaturation critical condition) is determined on the basis of the change in the fluorescence emission in response to the change in the denaturation condition.

The present invention also provides an apparatus for detecting denaturation of a nucleic acid which further comprises nucleic acid amplifying means for preparing a double-stranded nucleic acid to be examined.

More specifically, the present invention also provides an apparatus for detecting denaturation of a nucleic acid, comprising:

first nucleic acid amplifying means for separating a predetermined site of a first double-stranded nucleic acid to be examined into a first single-stranded nucleic acid and a second single-stranded nucleic acid to produce a large number of a third single-stranded nucleic acid and a sixth single-stranded nucleic acid, the fifth single-stranded nucleic acid comprising a base or nucleotide provided with a first label molecule and having a base sequence complementary to that of the first single-stranded nucleic acid, the sixth single-stranded nucleic acid having a base sequence complementary to that of the second single-stranded nucleic acid;

second nucleic acid amplifying means for separating a predetermined site of a second double-stranded nucleic acid as a reference, which is the same or substantially the same as the first double-stranded nucleic acid, into a third single-stranded nucleic acid which is the same or substantially the same as the first single-stranded nucleic acid, and a fourth single-stranded nucleic acid which is the same as or substantially the same as the second single-stranded nucleic acid, to produce a large number of a seventh single-stranded nucleic acid and an eighth single-stranded nucleic acid; the seventh single-stranded nucleic acid comprising a base or nucleotide provided with a second label molecule which is capable of causing energy transfer between itself and the first label molecule located within a predetermined distance, and having a base sequence complementary to that of the fifth single-stranded nucleic acid; the eighth single-stranded nucleic acid having a base sequence complementary to that of the fourth single-stranded nucleic acid;

nucleic acid mixing means for mixing the fifth single-stranded nucleic acid and the eighth single-stranded nucleic acid after the extraction thereof to produce a fifth double-stranded or partially double-stranded nucleic acid;

denaturation condition controlling means for controlling environment for denaturation under which the fifth double-stranded nucleic acid is separated into the fifth single-stranded nucleic acid and the eighth single-stranded nucleic acid;

excitation light irradiation means for emitting excitation light having a predetermined wavelength to irradiate the fifth double-stranded nucleic acid before denaturation, and the fifth single-stranded nucleic acid and eighth single-stranded nucleic acid after the denaturation, with the excitation light;

fluorescence detection means for detecting fluorescence emission based on the excitation light irradiation; and processing means for receiving, storing and processing a signal supplied from the fluorescence detection means;

whereby the fluorescence emitted from the nucleic acid is observed while changing the denaturation condition by the denaturation condition controlling means to measure the denaturation condition of the double-stranded nucleic acid.

The present invention further provides a method for detecting denaturation of a nucleic acid, comprising the steps of:

(a) supplying excitation light to a nucleic acid sample including a double-stranded nucleic acid which comprises a first single-stranded nucleic acid and a second single-stranded nucleic acid binding to the first single-stranded nucleic acid, thereby to measure fluorescence emitted from the nucleic acid sample before denaturation, the first single-stranded nucleic acid comprising a base provided with a first label molecule, the second single-stranded nucleic acid having a base sequence complementary to or substantially complementary to the first single-stranded nucleic acid and comprising a base provided with a second label molecule which is capable of causing energy transfer between itself and the first label molecule located within a predetermined distance;

(b) denaturing the nucleic acid sample to separate at least a portion of the double-stranded nucleic acid into the first and second single-stranded nucleic acids;

(c) supplying excitation light to the nucleic acid sample after the denaturation, thereby to measure fluorescence emitted from the nucleic acid sample after the denaturation; and (d) comparing the results of measurement of the fluorescence emitted from the nucleic acid sample before and after the denaturation, thereby to detect denaturation of the nucleic acid.

In the above-mentioned apparatus or method according to the present invention, a nucleic acid to be subjected to denaturation measurement may be prepared by hybridizing a single-stranded nucleic acid comprising a base or nucleotide labeled with an energy donor, with a single-stranded nucleic acid comprising a base or nucleotide labeled with an energy acceptor and having a base sequence complementary to the former single-stranded nucleic acid, and fluorescence having a predetermined wavelength emitted on the basis of the irradiation of the double-stranded nucleic acid with excitation light is detected and measured. In the present invention, there may be provided a difference in fluorescence characteristic such as wavelength-intensity distribution of the emitted fluorescence or lifetime of the emitted fluorescence, on the basis of a difference between a case wherein energy is transferred from the energy donor to the energy acceptor in a double-stranded state, and a case wherein substantially no energy is transferred from the energy donor to the energy acceptor since the double-stranded nucleic acid is denatured into a single-stranded state.

The apparatus for detecting denaturation of a nucleic acid according to the present invention may measure a characteristic value of the emitted fluorescence while controlling the denaturation condition of a double-stranded nucleic acid, and may detect a change in the characteristic of the fluorescence emitted from the nucleic acid, thereby to recognize the denaturation of the double-stranded nucleic acid and measure a predetermined value of the denaturation condition of the double-stranded nucleic acid to be measured.

More specifically, in the first apparatus for detecting denaturation of a nucleic acid according to the present invention, a double-stranded nucleic acid to be measured, which has been prepared in advance and comprises a single-stranded nucleic acid including a base labeled with a fluorescence energy donor, and a single-stranded nucleic acid including a base labeled with an energy acceptor and binding to the former single-stranded nucleic acid, is disposed or placed at a measuring point where the denaturation condition (such as temperature) may be controlled. An initial value of the denaturation condition is set at a predetermined value under which no denaturation will occur. Excitation light irradiation is conducted in this state to measure the fluorescence emitted from the sample. At this time, the quantity or amount to be measured may be: (1) the quantity of characteristic fluorescence emitted from the energy acceptor, (2) the quantity of characteristic fluorescence emitted from the energy donor, or (3) lifetime of fluorescence emitted from the energy donor.

Subsequently, the quantity to be measured is measured while changing the denaturation condition under the control of a processing unit, thereby to store the quantity to be measured at each of the denaturation condition values. After the measurement, denaturation point (denaturation critical condition) may be determined by utilizing at least one selected from: the degree of a decrease in the characteristic fluorescence emitted from the energy acceptor after the denaturation in a case where the quantity of the characteristic fluorescence emitted from the energy acceptor is measured; the degree of an increase in the characteristic fluorescence emitted from the energy donor in a case where the quantity of the characteristic fluorescence emitted from the energy donor is measured; and the degree of a change in the lifetime of fluorescence emitted from the energy donor in a case where the lifetime of the fluorescence is measured.

In the second apparatus for detecting denaturation of a nucleic acid according to the present invention, denaturation may be detected in a nucleic acid comprising a single-stranded nucleic acid to be examined and a reference single-stranded nucleic acid binding to the former nucleic acid, by utilizing a nucleic acid sample to be examined and a reference nucleic acid as starting materials. In this apparatus, one of the two species of the nucleic acids (i.e., reference nucleic acid sample and nucleic acid sample to be examined) is subjected to PCR amplification by using a base labeled with an energy donor molecule (or, is subjected to PCR amplification and then subjected to polymerization by using a base labeled with an energy donor molecule), and the other of the two species of the nucleic acids is subjected to PCR amplification by using a base labeled with an energy donor molecule (or, is subjected to PCR amplification and then subjected to polymerization by using a base labeled with an energy donor molecule). From the thus amplified nucleic acids, single-stranded nucleic acids, which are complementary to each other, are separately extracted or separated and then mixed to prepare a nucleic acid to be measured.

Subsequently, a denaturation point of the thus prepared nucleic acid to be measured may be determined by subjecting the nucleic acid to a measurement procedure in a similar manner as in the above-mentioned first apparatus for detecting denaturation of a nucleic acid.

Further objects and advantages of the present invention will be apparent from the description of the preferred embodiments with the accompanying drawings.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A1–1A2 and 1B1–1B2 are schematic views for illustrating an energy transfer phenomenon to be utilized in an apparatus for detecting denaturation of a nucleic acid according to the present invention.

FIG. 2 is a schematic sectional (partially perspective) view showing the structure of a first embodiment of the apparatus for detecting denaturation of a nucleic acid according to the present invention.

FIGS. 7A–7C are a schematic view for illustrating a method (former stage) of preparing a double-stranded nucleic acid to be measured.

FIGS. 9A1–9A3 and 9B are schematic views for illustrating a conventional method of detecting the denaturation of a nucleic acid.

DETAILED DESCRIPTION OF PREFERRED EMBODIMENTS

Prior to the description of preferred embodiments of the present invention, there is described an outline of the measurement principle in the apparatus and method for detecting denaturation of a nucleic acid according to the present invention.

Figure 2:
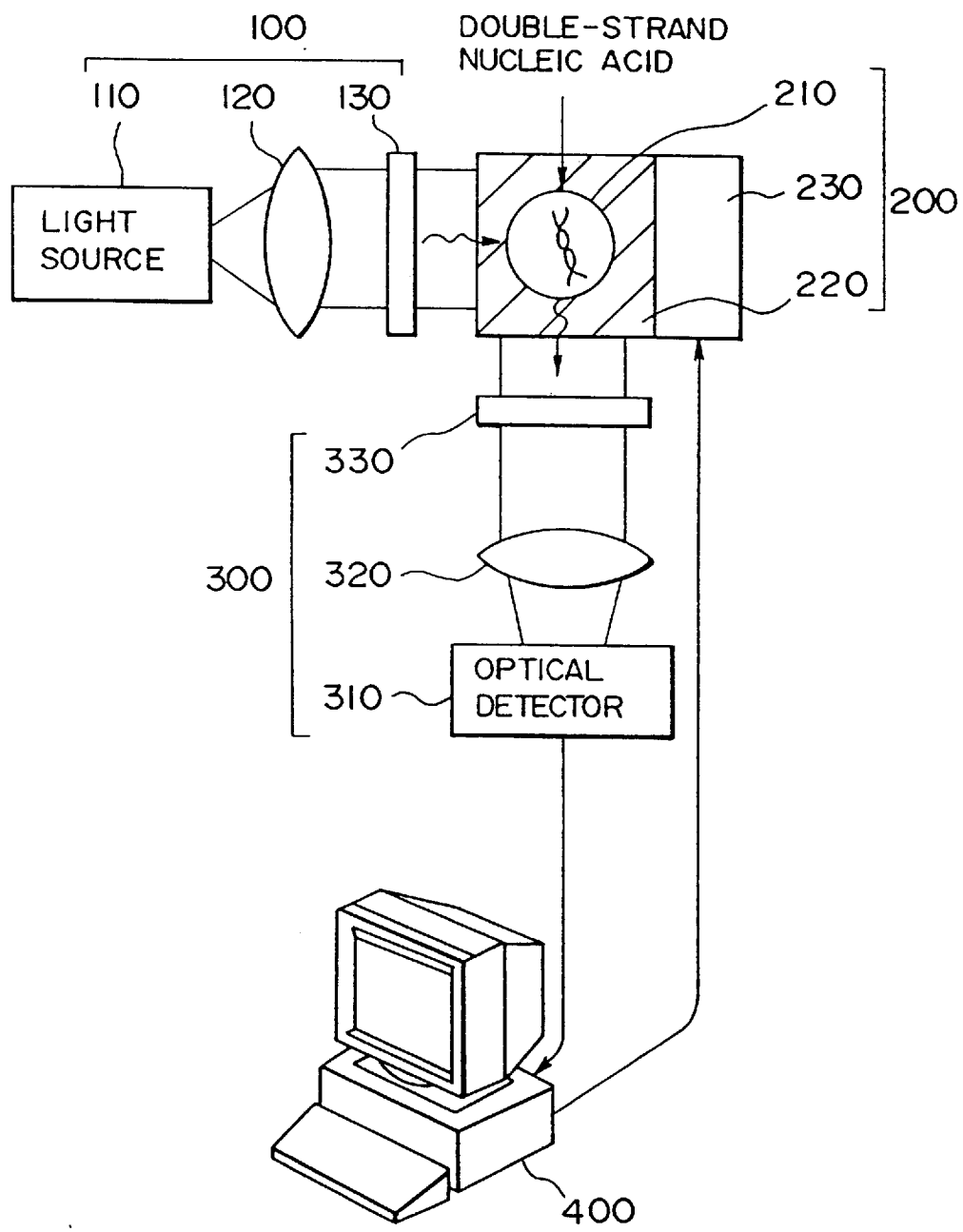

FIGS. 1A1–1A2 and 1B1–1B2 are schematic views for illustrating a phenomenon which is utilized for detecting the denaturation in a nucleic acid in the apparatus according to the present invention. As a fluorescent molecule capable of labeling or binding to the bases constituting a nucleic acid, there is known a combination of two species of fluorescent molecules which is capable of causing energy transfer when the distance between the two species of fluorescent molecules is 7 nm or smaller (L. Stryer: Ann. Rev. Biochem. 1978, vol.47, pp819–846). In addition, when a double-stranded nucleic acid is formed while providing an energy donor to one single-stranded nucleic acid and providing an energy acceptor to the other single-stranded nucleic acid, it is possible to form a pair in which the distance between the energy donor (D) and the energy acceptor (A) is approximately 2 nm in the double-stranded nucleic acid state as shown in FIGS. 1A1–1A2. In such a case, the average distance between the separated single-stranded nucleic acids (after the denaturation of the double-stranded nucleic acid) becomes much larger than 7 nm (i.e., the average distance capable of causing energy transfer between the single-stranded nucleic acids constituting a double-stranded nucleic acid).

When excitation light capable of causing a single energy donor to emit fluorescence is supplied to the above-mentioned double-stranded nucleic acid or single-stranded nucleic acid, the following phenomenon may occur.

(1) In the case of a double-stranded state before denaturation, energy is transferred from the energy donor supplied with the excitation light to the energy acceptor, and the energy acceptor emits fluorescence having a wavelength of $\lambda_A$ (hereinafter, such fluorescence is referred to as "$\lambda_A$ fluorescence").

(2) In the case of a single-stranded state after the denaturation, energy is not substantially transferred from the energy donor to the energy acceptor, and therefore only the energy donor emits fluorescence having a wavelength of $\lambda_D$ (hereinafter, such fluorescence is referred to as "$\lambda_D$ fluorescence").

FIGS. 1B1–1B2 show an intensity-wavelength distribution of the fluorescence emitted in a case where excitation light is supplied to the double-stranded nucleic acid state before denaturation, and an intensity-wavelength distribution of the fluorescence emitted in a case where excitation light is supplied to the single-stranded nucleic acid state after the denaturation. As shown in FIG. 1B1–1B2, when the intensities of the fluorescence before and after the denaturation are compared with each other, the intensity of the $\lambda_A$ fluorescence is decreased after the denaturation while the intensity of the $\lambda_D$ fluorescence is increased after the denaturation. In addition, while not shown in FIGS. 1B1–1B2, the lifetime of the $\lambda_D$ fluorescence is changed before and after the denaturation.

The apparatus (method) for detecting denaturation of a nucleic acid according to the present invention is an apparatus (method) for measuring a difference in the characteristic of the fluorescence emission before and after the denaturation as described above, thereby to detect the denaturation of a nucleic acid.

Hereinbelow, preferred embodiments of the present invention will be described with reference to the accompanying drawings. In these drawings, substantially the same or corresponding elements or components are denoted by the same or similar reference numerals, and redundant description thereof is omitted in the description relating to the drawings.

(First Embodiment)

FIG. 2 is a schematic view showing the structure of an apparatus for detecting denaturation of a nucleic acid according to a first embodiment of the present invention. In this apparatus, a fluorescein molecule is used as an energy donor and a rhodamine molecule is used as an energy acceptor, and the intensity (or frequency of emission occurrence) of a characteristic fluorescence ($\lambda_A$ fluorescence; wavelength=580 nm) emitted from the rhodamine is measured.

Referring to FIG. 2, this apparatus comprises: (a) an excitation light irradiation unit 100 for emitting excitation light having a predetermined wavelength to irradiate therewith a double-stranded nucleic acid before denaturation and a single-stranded nucleic acid after the denaturation (hereinafter, such double-stranded and single-stranded nucleic acid are comprehensively referred to as "nucleic acid to be measured");

(b) a denaturation condition controlling unit 200 for controlling an environment temperature as a denaturation condition of the nucleic acid to be measured;

(c) a fluorescence detecting unit 300 for detecting fluorescence emitted on the basis of the excitation light irradiation; and (d) a processing unit 400 for receiving, storing and processing a signal supplied from the fluorescence detecting unit 300 which provides an instruction concerning a set temperature to the denaturation condition controlling unit 200.

In FIG. 2, reference numeral 100 denotes an excitation light irradiation unit; 110, a light source; 120, a condenser lens; 130, a filter; 200, a denaturation condition controlling unit; 210, a container for a nucleic acid to be measured; 220, a thermally conducting material; 230, a variable heat source; 300, a fluorescence detecting unit; 310, a photodetector; 320, a condenser leans; 330, a filter; and 400, a processing unit.

The excitation light irradiation unit 100 used herein comprises: (1) a light source 110 for emitting light having a wavelength region including the wavelength of the excitation light, (2) a condenser lens 120 for concentrating the light emitted from the light source 110, and (3) a filter 130 for selectively transmitting light having a wavelength region including the wavelength of excitation light and a wavelength in the neighborhood thereof.

The denaturation condition controlling unit 200 comprises: (1) a container 210 for containing the nucleic acid to be measured, (2) a thermally conducting material 220 enclosing or surrounding the container 210, and (3) a variable heat source 230 for setting the temperature of the thermally conducting material 220 to a predetermined temperature in response to an instruction from outside. A part of the thermally conducting material 220 is made light-transmitting (inclusive of a vacant space or slit) so that the excitation light is incident to the nucleic acid to be measured contained in the container 210 through such a light-transmitting part, and the fluorescence emitted from the nucleic acid to be measured and propagating toward a specific direction is passed through the light-transmitting part. Further, as the variable heat source 230, a heater or the like may be used.

The fluorescence detecting unit 300 comprises: (1) a filter 330 for selectively transmitting light having a wavelength region including the wavelength of the $\lambda_A$ fluorescence and a wavelength in the neighborhood thereof, (2) a condenser lens 320 for concentrating light transmitting through the filter 330, and (3) a photodetector 310 for receiving light passing through the condenser lens 320 to convert the light into an electric signal.

In the apparatus as shown in FIG. 2, denaturation of a nucleic acid may be detected in the following manner.

First, a nucleic acid to be measured is prepared and charged into the container 210. At this time, the set temperature based on the instruction from the processing unit 400 to the denaturation condition controlling unit 200 may be such that it provides a temperature in the container 210 at which the nucleic acid to be measured is not denatured. In this state, the excitation light irradiation unit 100 is driven to supply excitation light to the nucleic acid to be measured. The fluorescein molecule provided to the nucleic acid to be measured which has been irradiated with the excitation light makes a transition to an excited state.

In a case where no rhodamine molecule is present within a distance of 7 nm from the fluorescein molecule in the excited state, the fluorescein molecule emits the characteristic fluorescence ($\lambda_D$ fluorescence; wavelength=520 nm) and makes a transition to the ground state. On the other hand, in a case where a rhodamine molecule is present within a distance of 7 nm from the fluorescein molecule in the excited state, energy is transferred from the fluorescein molecule functioning as an energy donor to the rhodamine molecule functioning as an energy acceptor. When such energy transfer occurs, the fluorescein molecule makes a transition to the ground state without emitting the $\lambda_D$ fluorescence, and the rhodamine molecule makes a transition to the excited state and thereafter makes a transition to the ground state while emitting the $\lambda_A$ fluorescence.

The thus emitted $\lambda_A$ fluorescence is transmitted through the filter 330, and then inputted to the photodetector 310 through the condenser lens 320. The photodetector 310 detects the light upon receipt thereof, and converts it into an electric signal to output the resultant electric signal to the processing unit 400. The processing unit 400 receives a light reception signal supplied from the photodetector 310 and stores the signal together with the above-mentioned set temperature.

Then, the processing unit 400 instructs the denaturation condition controlling unit 200 to change the set temperature to a higher temperature than that in the preceding measurement. In this state, the excitation light irradiation unit 100 is driven to supply excitation light to the nucleic acid to be measured, and the $\lambda_A$ fluorescence emission is measured in the same manner as described above. At this time, the processing unit 400 receives the light reception signal supplied from the photodetector 310 and stores the signal together with the set temperature after the above-mentioned temperature change.

Subsequently, while the set temperature of the denaturation condition controlling unit 200 is successively increased according to instructions given by the processing unit 400, the $\lambda_A$ fluorescence emitted from the nucleic acid is measured at each of set temperatures. The light reception signal supplied from the photodetector 310 under a condition corresponding to each of set temperatures is inputted to the processing unit 400 and stored therein together with the corresponding set temperature.

Figure 3A:
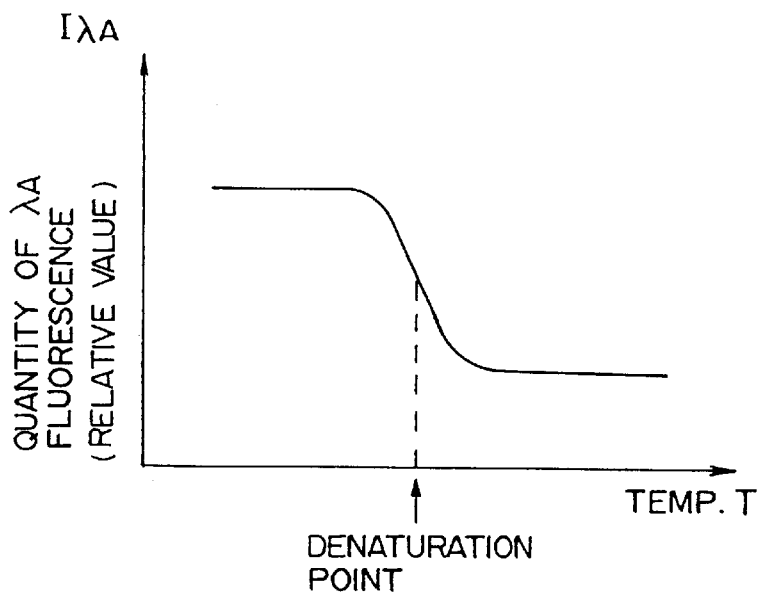
FIGS. 3A and 3B are schematic views for illustrating the detection of a denaturation point utilizing the measurement of a $\lambda_A$ fluorescence (i.e., fluorescence emitted from an energy acceptor) intensity.
Figure 3B:
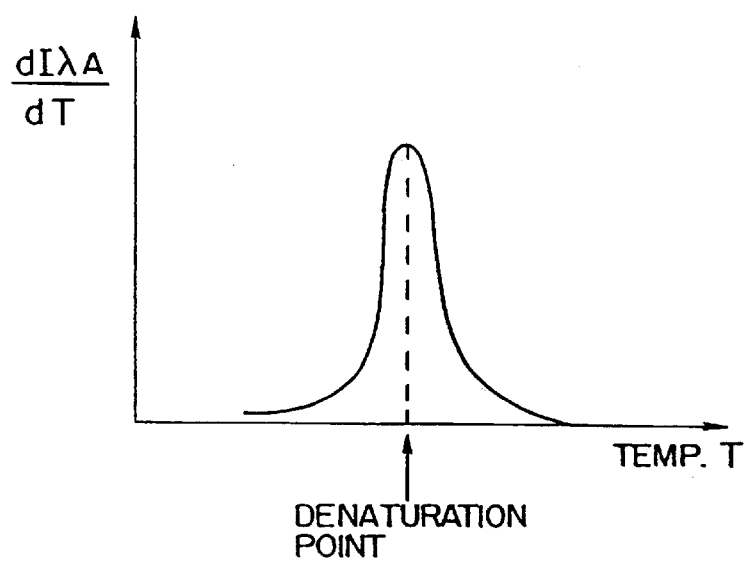

FIGS. 3A and 3B are views each showing results of measurement obtained through the above-mentioned measurement procedure. FIG. 3A is a graph obtained by plotting the contents or data stored in the processing unit 400. In FIG. 3A, the abscissa represents temperature and the ordinate represents the intensity of $\lambda_A$ fluorescence (or frequency of the $\lambda_A$ fluorescence detection). FIG. 3B is a graph obtained by plotting the temperature data (abscissa) and differential value of the $\lambda_A$ fluorescence intensity with respect to temperature (ordinate), on the basis of the data as shown in FIG. 3A.

As shown in FIG. 3A, the $\lambda_A$ fluorescence intensity before the denaturation is stronger than the $\lambda_A$ fluorescence intensity after the denaturation and is abruptly changed at a specific temperature or in the neighborhood thereof. The temperature at which such an abrupt change occurs is detected as a denaturation point. Alternatively, when the differential value of the $\lambda_A$ fluorescence intensity with respect to temperature is calculated on the basis of the above-mentioned stored data, a graph as shown in FIG. 3B may be obtained. In such a case, the denaturation point may also be determined as the largest absolute value of the differential value.

Figure 4A:
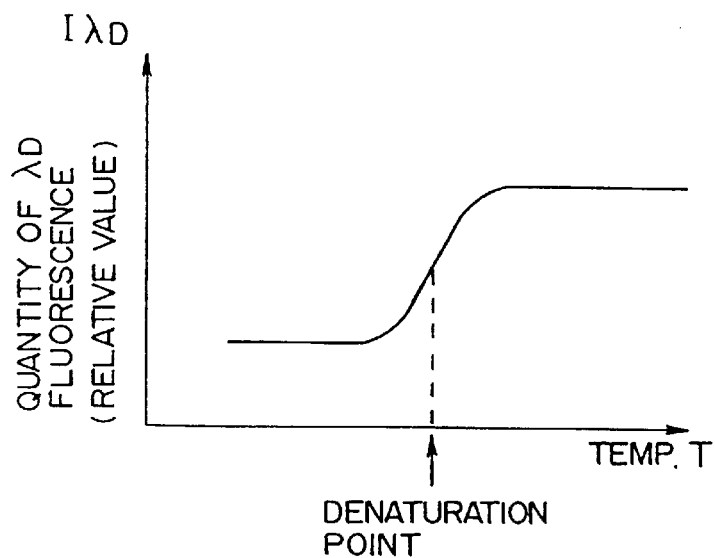
FIGS. 4A and 4B are schematic views for illustrating the detection of a denaturation point utilizing the measurement of a $\lambda_D$ fluorescence (i.e., fluorescence emitted from an energy donor) intensity.
Figure 4B:
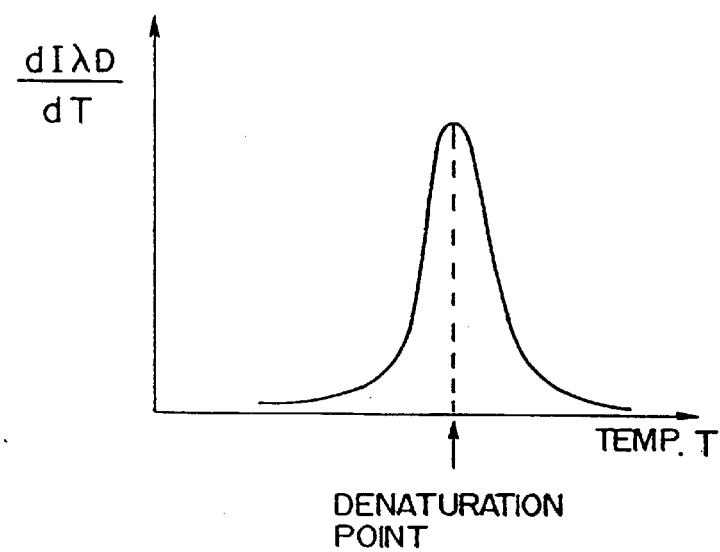

In this embodiment, the value or amount to be measured may also be the intensity of the $\lambda_D$ fluorescence. In such a case, measurement may be conducted in the same manner as described above except for using a filter having a transmittance wavelength band including the wavelength of the $\lambda_D$ fluorescence or in the neighborhood thereof as the filter 330. FIGS. 4A and 4B are views each showing the results of measurement obtained through such a measurement procedure. FIG. 4A is a graph obtained by plotting the contents or data stored in the processing unit 400. In FIG. 4A, the abscissa represents temperature and the ordinate represents the intensity of $\lambda_D$ fluorescence (or frequency of the $\lambda_A$ fluorescence detection). FIG. 4B is a graph obtained by plotting the temperature data (abscissa) and differential value of the $\lambda_D$ fluorescence intensity with respect to temperature (ordinate), on the basis of the data as shown in FIG. 4A.

As shown in FIG. 4A, the $\lambda_D$ fluorescence intensity before the denaturation is weaker than the $\lambda_D$ fluorescence intensity after the denaturation and is abruptly changed at a specific temperature or in the neighborhood thereof. The temperature at which such an abrupt change occurs is detected as a denaturation point. Alternatively, when the differential value of the $\lambda_D$ fluorescence intensity with respect to temperature is calculated on the basis of the above-mentioned stored data, a graph as shown in FIG. 4B may be obtained. In such a case, the denaturation point may also be determined as the largest absolute value of the differential value.

In this embodiment, the value or amount to be measured may also be the lifetime of the fluorescence (e.g., the lifetime of the $\lambda_D$ fluorescence). In such a case, measurement may be conducted in the same manner as described above except that a filter having a transmittance wavelength band including the wavelength of the $\lambda_D$ fluorescence or in the neighborhood thereof is used as the filter 330, and an optical waveform measuring device such as streak camera is used as the photodetector 310. In such a case, the processing unit 400 stores the values of fluorescence lifetime together with the set temperature.

Figure 5A:
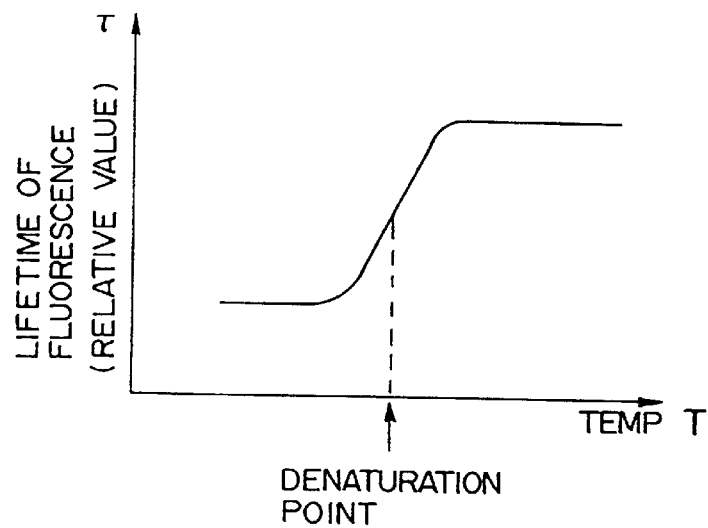
FIGS. 5A and 5B are schematic views for illustrating the detection of a denaturation point utilizing the measurement of fluorescence lifetime.
Figure 5B:
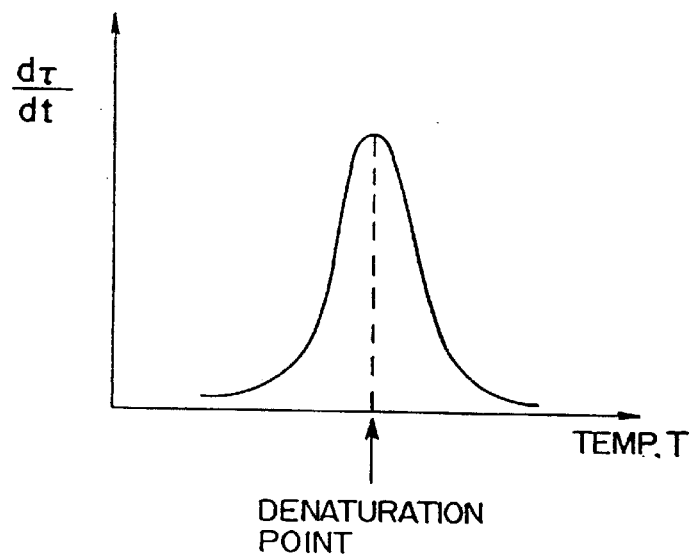

FIGS. 5A and 5B are views each showing the results of measurement obtained through such a measurement procedure. FIG. 5A is a graph obtained by plotting the contents or data stored in the processing unit 400. In FIG. 5A, the abscissa represents temperature and the ordinate represents the lifetime of the fluorescence ($\lambda_D$ fluorescence) emitted from the energy donor. FIG. 5B is a graph obtained by plotting the temperature data (abscissa) and differential value of the lifetime of fluorescence ($\lambda_D$ fluorescence) emitted from the energy donor with respect to temperature (ordinate), on the basis of the data as shown in FIG. 5A.

As shown in FIG. 5A, the average lifetime of the fluorescence before the denaturation is larger than the average lifetime of fluorescence after the denaturation and is abruptly changed at a specific temperature or in the neighborhood thereof. The temperature at which such an abrupt change occurs is detected as a denaturation point. Alternatively, when the differential value of the fluorescence lifetime with respect to temperature is calculated on the basis of the above-mentioned stored data, a graph as shown in FIG. 5B may be obtained. In such a case, the denaturation point may also be determined as the largest absolute value of the differential value.

(Second Embodiment)

Figure 6:
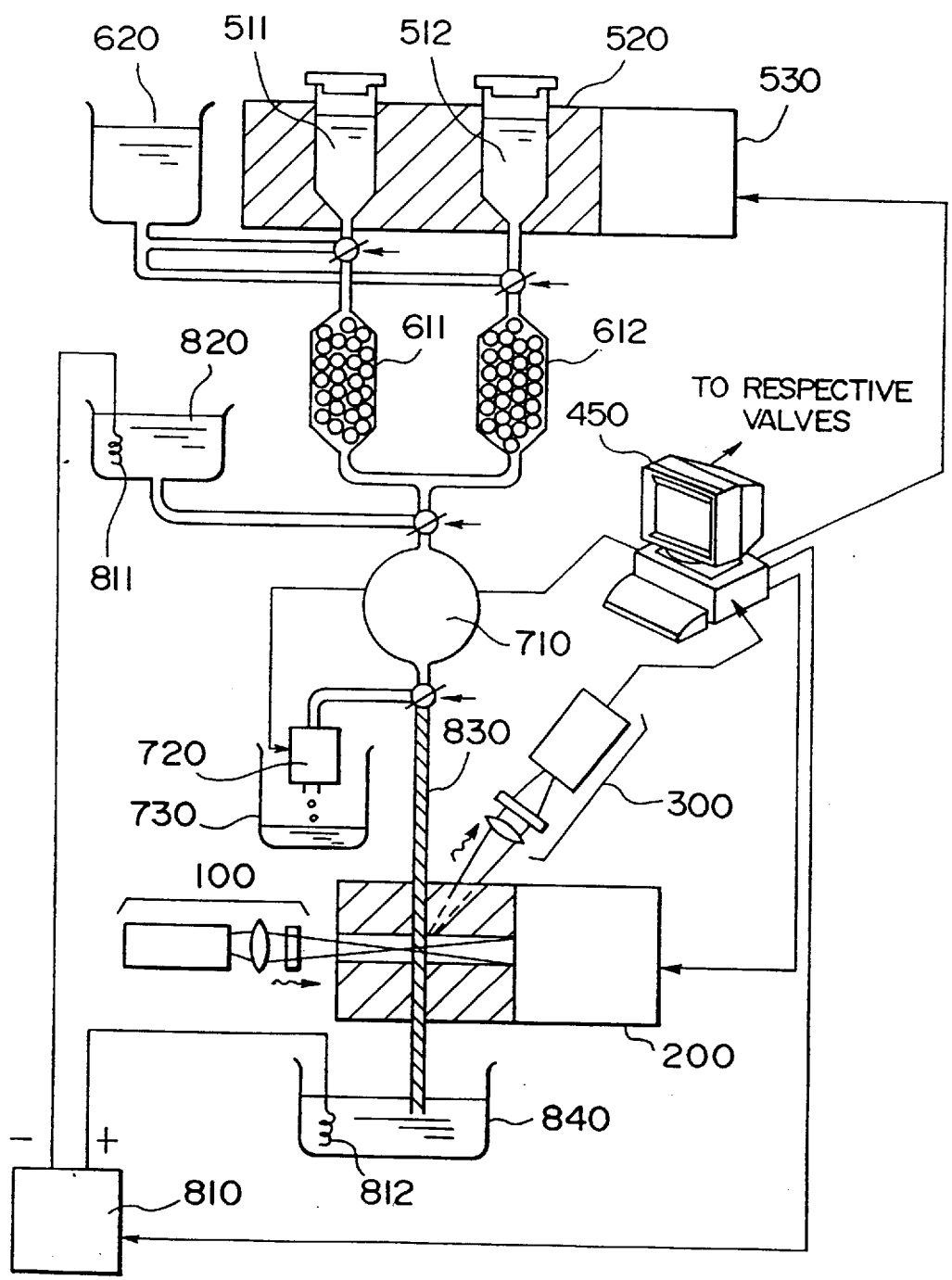
FIG. 6 is a schematic sectional (partially perspective) view showing the structure of a second embodiment of the apparatus for detecting denaturation of a nucleic acid according to the present invention.

FIG. 6 is a schematic view showing the structure of an apparatus for detecting denaturation of a nucleic acid according to a second embodiment of the present invention. In the above-mentioned first embodiment, a nucleic acid prepared in advance is used as the nucleic acid to be measured. On the other hand, an apparatus according to this embodiment is one for detecting denaturation of a nucleic acid to be measured which may be prepared by combining or hybridizing a nucleic acid sample to be examined and a reference (or probe) nucleic acid sample as starting materials. More specifically, in this embodiment, the nucleic acid to be measured comprises the nucleic acid to be examined in a single-stranded form and the reference nucleic acid in a single-stranded form binding to the nucleic acid to be examined. Similarly as in the first embodiment described above, a fluorescein molecule is used as an energy donor and a rhodamine molecule is used as an energy acceptor.

More specifically, the apparatus according to this embodiment comprises:

(a) a nucleic acid amplifying unit for preparing a sample comprising a predetermined portion of a reference double-stranded nucleic acid and a portion a double-stranded nucleic acid to be examined which corresponds to the predetermined portion, and then PCR-amplifying one of these double-stranded nucleic acids by using a base or nucleotide provided or labeled with a fluorescein molecule, and PCR-amplifying the other of these double-stranded nucleic acids by using a base provided with a rhodamine molecule;

(b) an extracting unit for extracting, with respect to these two species of the double-stranded nucleic acids amplified by the above-mentioned nucleic acid amplifying unit, a single-stranded nucleic acid forming one of the two species of double-stranded nucleic acids, and a single-stranded nucleic acid which is in a complementary relation with the above-mentioned single-stranded nucleic acid from the other of the two species of double-stranded nucleic acids;

(c) a mixing unit for receiving the two species of the single-stranded nucleic acids extracted by the extracting unit and mixing the two species of the single-stranded nucleic acids to produce a nucleic acid to be measured while mixing the nucleic acid to be measured with a gel carrier;

(d) a gel electrophoresis unit for leading or introducing the nucleic acid to be measured produced by the mixing unit to a measurement point;

(e) an excitation light irradiation unit 100 for emitting excitation light having a predetermined wavelength to irradiate a double-stranded nucleic acid before denaturation or a single-stranded nucleic acid after the denaturation, with the excitation light;

(f) a denaturation condition controlling unit 200 for controlling an environment temperature of the nucleic acid to be measured as a denaturation condition;

(g) a fluorescence detection unit 300 for detecting fluorescence emission based on the irradiation of the nucleic acid with the excitation light; and (h) a processing unit 450 for giving an instruction for a set temperature to the denaturation condition control unit 200 to control the operation of the entire apparatus, and for receiving, storing and processing a signal supplied from the fluorescence detecting unit 300.

In FIG. 6, reference numeral 450 denotes a processing unit; 511, 512, containers for PCR-amplification; 520, a thermally conducting unit; 530, a variable heat source; 611, 612, containers for absorbing materials; 620, a container for an eluent denaturant; 710, a mixing vessel; 720, a pump; 730, a container for discharged solution; 810, a power source; 811, 812, electrodes; 820, 840, containers for a gel carrier; and 830, a column.

The above-mentioned nucleic acid amplifying unit comprises: (1) a container 511 for containing a reference nucleic acid sample and a base provided with a fluorescein molecule, (2) a container 512 for containing a nucleic acid to be examined and a base provided with a rhodamine molecule, (3) a thermally conducting material 520 for surrounding or enclosing the containers 511 and 512, and (4) a variable heat source 530 for setting the temperature of the thermally conducting material 520 to a designated temperature in response to an instruction from outside.

The extracting unit comprises: (1) a container 611 connected to the container 511 through a valve, for containing a matrix material having a surface to which avidin is attached, (2) a container 612 connected to the above container 512 through a valve, for containing a matrix material having a surface to which the avidin is attached, and (3) a container 620 connected to the above container 611 and container 612 through respective valves, for containing formamide (80%) which is an extracting solution having a function of a denaturant or denaturing agent.

The mixing unit comprises: (1) a mixing vessel 710 connected to the above container 611 and container 612 through respective valves, for mixing the two species of extracted single-stranded nucleic acids, (2) a pump 720 connected to the mixing vessel 710 through a valve, for discharging a solution in the mixing vessel 710, and (3) a container 730 for containing the solution discharged from the pump 720.

The gel electrophoresis unit comprises: (1) a power supply 810 for supplying an application voltage, (2) a negative electrode 811 connected to the power supply 810, (3) a positive electrode 812 connected to the power supply 810, (4) a container 820 connected to the mixing vessel 710 through a valve, for containing a gel carrier, (5) a column 830 in a capillary or slender tube form, one end of which is connected to the mixing vessel 710 through a valve, and (6) a container 840 disposed in the other end side of the column 830, for containing the gel carrier.

In this embodiment, the excitation light irradiation unit 100, the denaturation condition controlling unit 200 and the fluorescence detecting unit 300 have the same structure or constitution as those constituting the first embodiment as described above. The processing unit 450 has, in addition to the components constituting the processing unit 400 in the first embodiment, an amplification controlling function to give an instruction for a set temperature to the nucleic acid amplifying unit and a function of controlling the valves disposed in the apparatus, and supplies control signals to these components (inclusive of the valves).

In the apparatus shown in FIG. 6, first, a nucleic acid to be measured is prepared. FIGS. 7A–7C and 8A–8C are schematic views for illustrating a procedure for preparing a nucleic acid to be measured from a reference nucleic acid sample and a nucleic acid sample to be examined. With reference to these Figures, operation of preparing the nucleic acid to be measured is described below.

Referring to FIGS. 7A–7C, two species of primers are respectively caused to contact the reference nucleic acid and the nucleic acid to be examined to produce a reference nucleic acid sample and a nucleic acid sample to be examined respectively including predetermined sites. At this time, biotin is provided to one of these primers to bind to the reference nucleic acid and biotin is provided to the other of these primers to bind to the nucleic acid to be examined.

With respect to the thus produced samples, the reference nucleic acid sample is subjected to PCR-amplification in the container 511 containing a solution comprising fluorescein-dUTP, and the nucleic acid sample to be examined is subjected to PCR-amplification in the container 512 containing a solution comprising rhodamined-UTP, respectively, under temperature control using the variable heat source 530 controlled by the processing unit 450 through the thermally conducting material 520. As a result, there are produced a large amount of reference nucleic acid comprising a base provided with the fluorescein and the nucleic acid to be examined composing a base provided with the rhodamine, as shown in FIG. 7B.

Each of the amplified nucleic acids is introduced into the container 611 or the container 612 under valve control conducted by the processing unit 450. At this time, a predetermined site provided with the biotin is coupled with the avidin provided to the matrix material preliminarily contained in the container 611 and 612, and remains in the containers 611 and 612. However, the other component not provided with the biotin is passed through the containers 611 and 612, as shown in FIGS. 7A–7C and FIGS. 8A–8C. The solution having passed through the containers is stored in the mixing vessel 710 and then discharged through the pump 720 to the container 730 in response to an instruction from the processing unit 450.

Figure 8A:
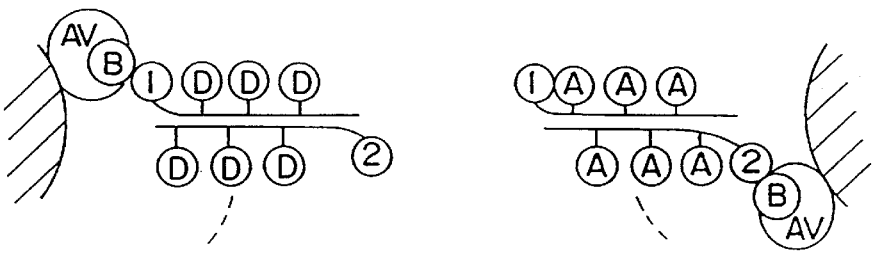
FIGS. 8A–8C are a schematic view for illustrating a method (latter stage) of preparing a double-stranded nucleic acid to be measured.
Figure 8B:
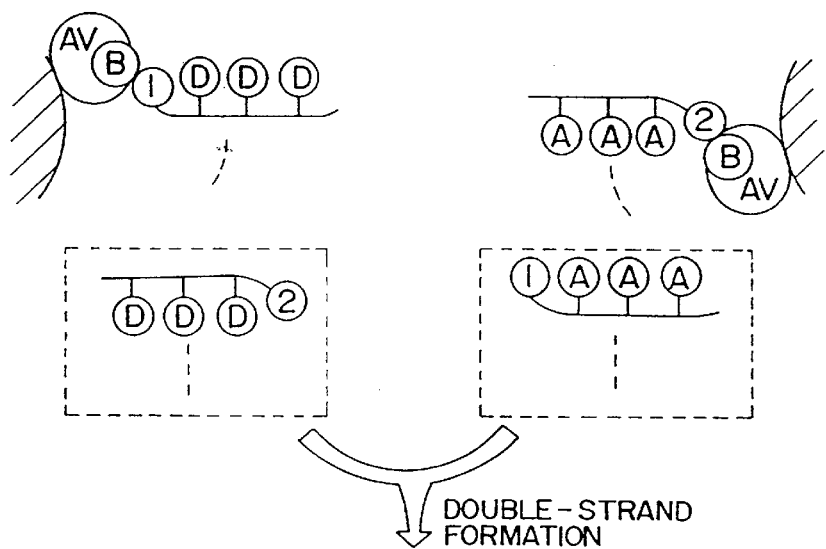
Figure 8C:
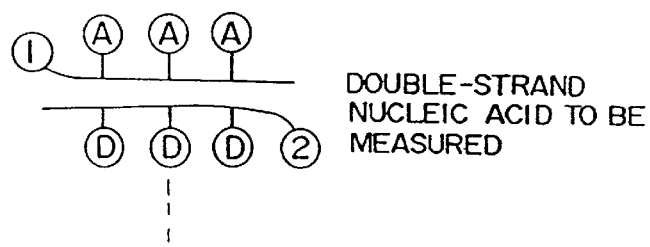

Then, the formamide (80%) is introduced into the containers 611 and 612 from the container 620, and a single-stranded nucleic acid at the primer side not provided with the biotin is eluted as shown in FIG. 8B. The eluted single-stranded nucleic acid is introduced into the mixing vessel 710 under valve control conducted by the processing unit 450, and is subjected to annealing after the mixing, thereby to provide a nucleic acid to be measured, as shown in FIG. 8C. At this time, the gel carrier is introduced into the mixing vessel 710 and the column 830.

Under the application of a voltage from the power supply 810, the nucleic acid to be measured is moved through the mixing vessel 710 and the column 830 to the measurement point where the denaturation condition controlling unit 200 is disposed. Subsequently, the characteristic fluorescence from the nucleic acid is measured in the same manner as in the first embodiment as described above, thereby to detect the denaturation thereof.

The present invention is not limited to the above mentioned specific embodiments but various modifications thereto may also be possible. For example, while temperature is used as the denaturation condition in the above-mentioned embodiments, the concentration of a denaturing agent such as formamide may also be a denaturation condition and such a concentration may be changed gradually or stepwise. In addition, the energy donor and the energy acceptor are not limited to a combination of fluorescein and rhodamine. Alternatively, such a combination of an energy donor and an energy acceptor having different characteristic fluorescence wavelength may be used as long as energy transfer occurs therebetween. In addition, the method of preparing the nucleic acid to be measured in the second embodiment is an example, and any of other known methods for the preparation of a nucleic acid to be measured may also be used.

Hereinbelow, the present invention will be described in more detail with reference to specific Examples.

EXAMPLES

Purified DATP, dCTP, dGTP, and dTTP in solution were obtained from Pharmacia, and Fluorescein-11-dUTP (FluoroGreen) and Rhodamine-4-dUTP (FluoroRed) were obtained from Amersham. The pBluescript II DNA used was obtained from STRATAGENE. AMPUTAQ™ DNA polymerase was obtained from Perkin Elmer Cetus. Formamide (ultra-pure grade) was obtained from International Biotechnologies, Inc.

Example 1
(Fluorescent label incorporation during PCR)

PCR amplification of fluorophore-labeled DNA was conducted basically in the same manner as described by Woolford and Dale (Woolford, A. J., and Dale, J. W.; (1992) FEMS Microbiology Letters 99, 311–316) with some modifications. The target fragment used in this Example was the multi-cloning site of pBluescript II. PCR primers for amplification used herein were the M13 reverse and M13 (−20) forward primers, one of which had been biotinylated for further purification. A PCR reaction mixture used herein was 10 mM Tris-HCl (pH 8.3), 50 mM KCl, 1.5 mM $MgCl_2$, 250 $\mu M$ each of DATP, dCTP, dGTP, 33 $\mu M$ dTTP, 2 nmol of either Fluorescein-11-dUTP (FluoroGreen) or Rhodamine-4-dUTP (FluoroRed), 10 ng pBluescript II DNA, 20 pmol of each primer, and 0.2 $\mu l$ (1 unit) of AMPLITAQ DNA polymerase, making up a total volume of 50 $\mu l$. PCR was conducted by initial incubation at 94° C. for 1 min, followed by 30 cycles of 41° C. for 1 min, 72° C. for 2 min, and 94° C. for 1 min, and final incubation of 41° C. for 5 min, and 72° C. for 7 min.

Example 2
(Preparation of fluorophore-labeled double-strandeded DNA)

To separate the PCR product obtained in Example 1 from unincorporated fluorescent-dUTP and to obtain single-strandeded DNAs, magnetic beads with covalently coupled streptavidin (DYNABEADS™ M-280 streptavidin, DYNAL, Oslo, Norway) were used (Hultman, T. ,Ståhl, S., Hornes, E., and Uhlén, M.; (1989) Nucleic Acids Research 17, 4937–4946.12).

The PCR product obtained in Example 1 was first immobilized on the magnetic beads, and thereafter the beads were washed as described in the manufacturer's instruction manual accompanying the above-mentioned "Dynabeads M-280 streptavidin". Then, single-strandeded DNA was obtained by incubating the immobilized products (beads) in 200 $\mu l$ of 0.15N NaOH for 15 min, and recovered into the resultant supernatant. The supernatant, including the resultant single-strandeded DNA was neutralized with aliquots of 1N HCl and 1M Tris-HCl (pH 8.0) (final concentrations of 150 mM NaCl and 10 mM Tris-HCl) in heat denaturation experiments and with aliquots of 1N HCl and glycine buffer [125 mM glycine, 125 mM $Na_2HPO_4$, (pH 8.3)] (final concentrations of 150 mM NaCl and 62.5 mM glycine/ $Na_2HPO_4$) in alkali denaturation experiments.

Figure 10:
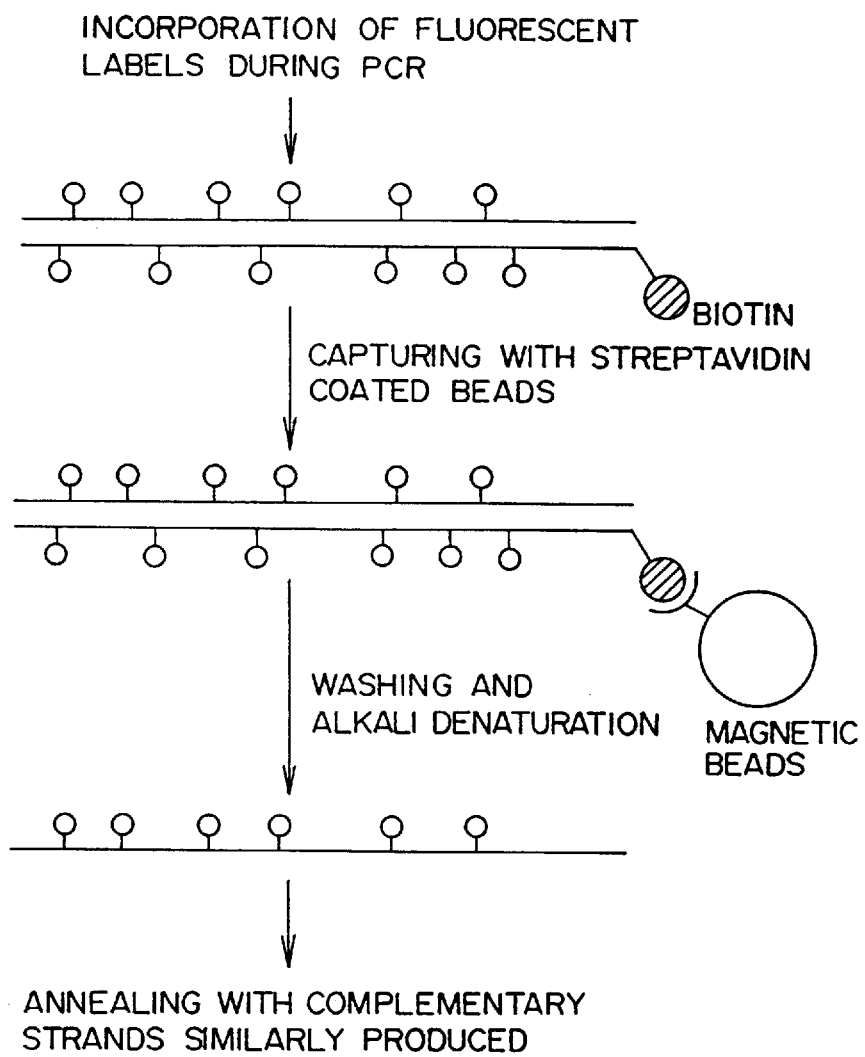
FIG. 10 is a schematic diagram for illustrating PCR-driven fluorescent label incorporation used in Examples appearing hereinafter.

The single strands thus obtained were interchain-labeled with fluorescein (energy donor) or rhodamine (energy acceptor) and were complementary to each other, as shown in FIG. 10. FIG. 10 shows PCR-driven fluorescent label incorporation wherein with one of the primer pair biotinylated on the 5'-terminus, the target DNA fragments are amplified by polymerase chain reaction (PCR). The fragments are captured on streptavidin-coated magnetic beads and non-biotinylated strands are eluted.

In this Example, fluorescein-labeled strands (stranded-F) and rhodamine-labeled strands (stranded-R) were mixed and annealed at 65° C. for 30 min, thereby to provide fluorophore-labeled double-strandeded DNA.

Example 3
(DNA denaturation and FRET assay)

Heat denaturation of the labeled and annealed samples obtained in Example 2 was monitored after the samples were heated in an aluminum block (Model TAL-1G, TAITEC) for 15 min and cooled immediately with ice to 20° C. The heating temperature was increased in 5 degree increments over the range from 65° C. to 95° C. For denaturation by alkaline pH, the pH of the annealed samples was simply increased gradually by adding aliquots of 1N NaOH and the fluorescence was measured each time.

Fluorescence Resonance Energy Transfer (FRET) is manifested as three main effects (Tsien, R. Y., Bacskai, B. J., and Adams, S. R.; (1993) Trends in Cell Biology 3, 242–245): (I) reduction in the fluorescence intensity of the donor fluorophore, (II) reduction in the life-time of excited state, and (III) re-emission of fluorescence by the acceptor molecule at a longer wavelength. Loss of the donor brightness is the most easily measured effect but it is also often the most vulnerable to confounding artifacts such as bleaching or other physical loss of donor fluorophores. By picosecond life-time spectrofluorometry, it is possible to measure the excited-state life-times directly (Kusumi, A., Tsuji, A., Murata, M., Sako, Y., Yoshizawa, A. C., Kagiwada, S., Hayakawa, T., and Ohnishi, S.; (1991) Biochemistry 30, 6517–6527).

Figure 11:
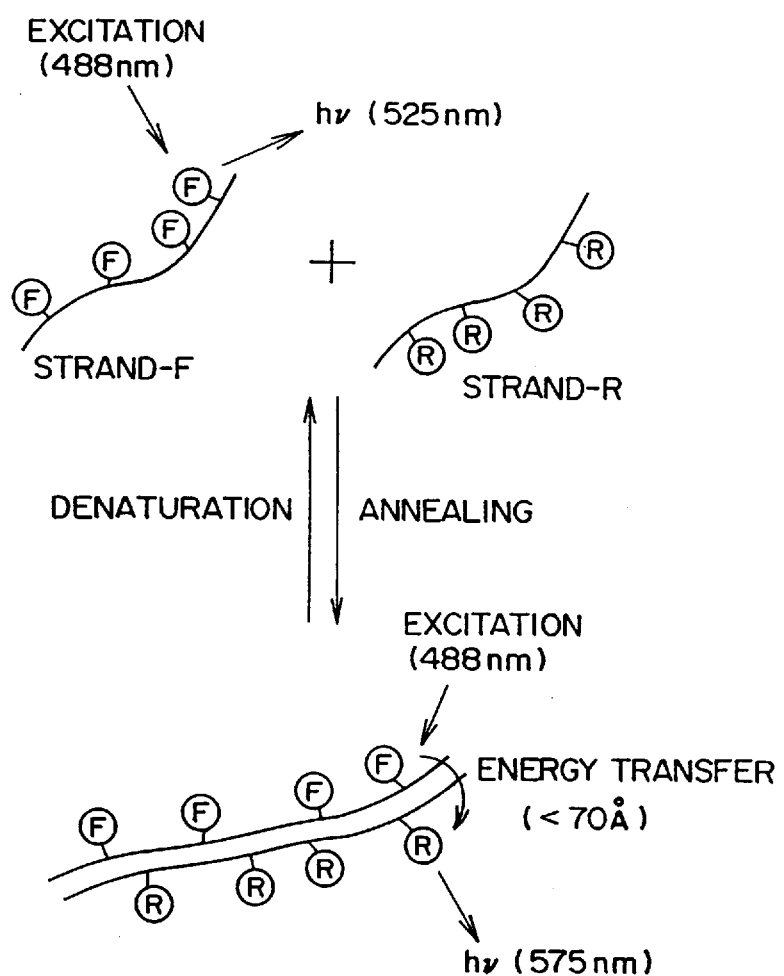
FIG. 11 is a schematic diagram for illustrating fluorescence resonance energy transfer (FRET) upon DNA hybridization used in Examples appearing hereinafter.

FIG. 11 shows FRET upon DNA hybridization, wherein after annealing, FRET occurs between the stranded-F with energy donors (F) and the stranded-R with energy acceptors (R). FRET is disrupted by denaturation. Fluorescein as the energy donor absorbs light at 488 nm and its emission peak is present at 525 nm. Rhodamine as the energy acceptor fluoresces at longer wavelengths around 575 nm.

In this Example, FRET was monitored by measuring the ratio of the fluorescence emissions from the donor (fluorescein) and the acceptor (rhodamine) during continuous donor excitation. The fluorescence emission spectra and fluorescence intensities at fixed wavelengths were measured by using a commercially available spectrofluorometer (Model F-4010, HITACHI) with the temperature of the measuring cuvette maintained at 20° C.

Samples were excited at 488 nm (5 nm slit width) and the accompanying green (525 nm) and red (575 nm) emissions were measured. The ratio of the emissions (525 nm/575 nm) reflects the efficiency of the energy transfer. When the energy transfer increases, the ratio of the emissions (525 nm/575 nm) decreases.

RESULTS
<Fluorophore-labeled double-strandeded DNA preparation for optimal FRET assay>

In the above Example, PCR-amplified and fluorophore-labeled DNA was immobilized on magnetic beads and recovered as single-strandeded DNA by alkali denaturation. For estimation of the amount of the resultant products, the fluorescence intensities of the fluorescein-labeled strands (stranded-F) and the rhodamine-labeled strands (stranded-R) were, after neutralization, measured separately at different combinations of excitation and emission wavelengths: 488 nm/525 nm for the stranded-F, and 540 nm/575 nm for the stranded-R.

Figure 12:
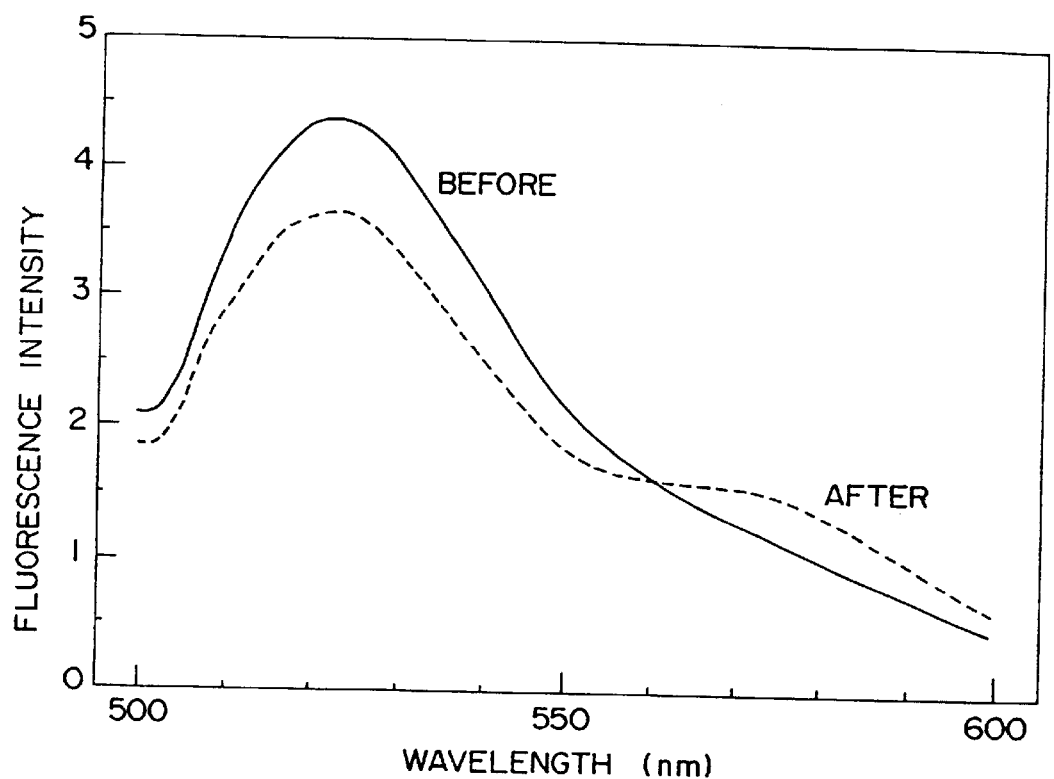
FIG. 12 is a graph showing fluorescent emission spectra of a mixture of complementary strands before and after annealing.

FIG. 12 shows a spectral change due to disruption and the occurrence of FRET. The fluorescence of a mixture of the stranded-R and the stranded-F was first measured at 20° C. before annealing as shown by the solid line in the graph of FIG. 12. The excitation wavelength was 488 nm. The strands were annealed in 0.15M NaCl and 0.1M Tris-HCl (pH 8.0) at 65° C. for 30 min, and cooled to 20° C.

The fluorescence emission spectrum and the fluorescence intensity ratio were measured again and an enhancement of the energy transfer on base pairing was found, as shown by the dotted line in the graph of FIG. 12.

Figure 13:
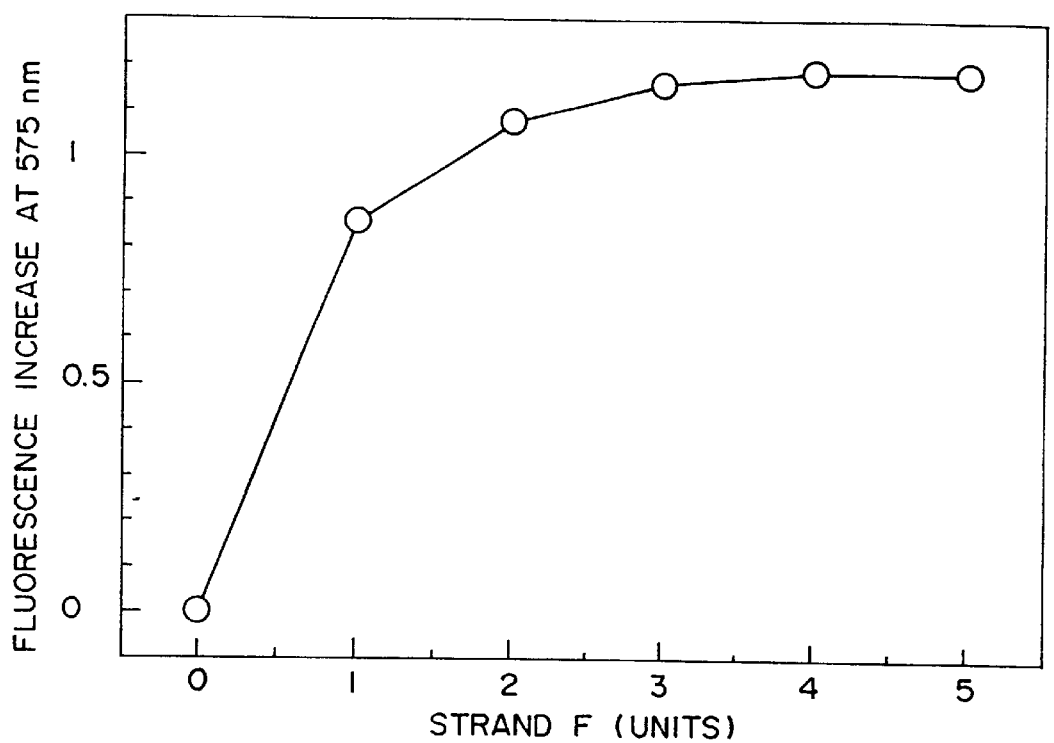
FIG. 13 is a graph showing the optimization of the ratio of fluorescein-labeled stranded (stranded-F) and rhodamine-labeled stranded (stranded-R).

Theoretically, when equimolar strands are annealed, the efficiency of energy transfer should be maximum. However, because the concentrations of the strands and fluorophores were unknown in these preparations, the optimum annealing ratio was determined empirically. One to five units (in terms of arbitrary or relative fluorescence intensity) of stranded-F were annealed to five units of stranded-R, and the changes in the fluorescence spectra were observed. The observation results are shown in FIG. 13. In FIG. 13, one to five units of the stranded-F were annealed to five units of the stranded-R at 65° C. for 30 min. The annealing mixture contained 0.15M NaCl and 0.1M Tris-HCl (pH 8.0). The fluorescence increase at 575 nm was monitored in a similar manner as in that for FIG. 12.

As shown in FIG. 13, the ratio of 525 nm/575 nm became a maximum, when four units of the stranded-F were used. Henceforth, the stranded-R/stranded-F ratio of 5/4 was used in the following denaturation experiments.

<FRET in heat denaturation>

Figure 14:
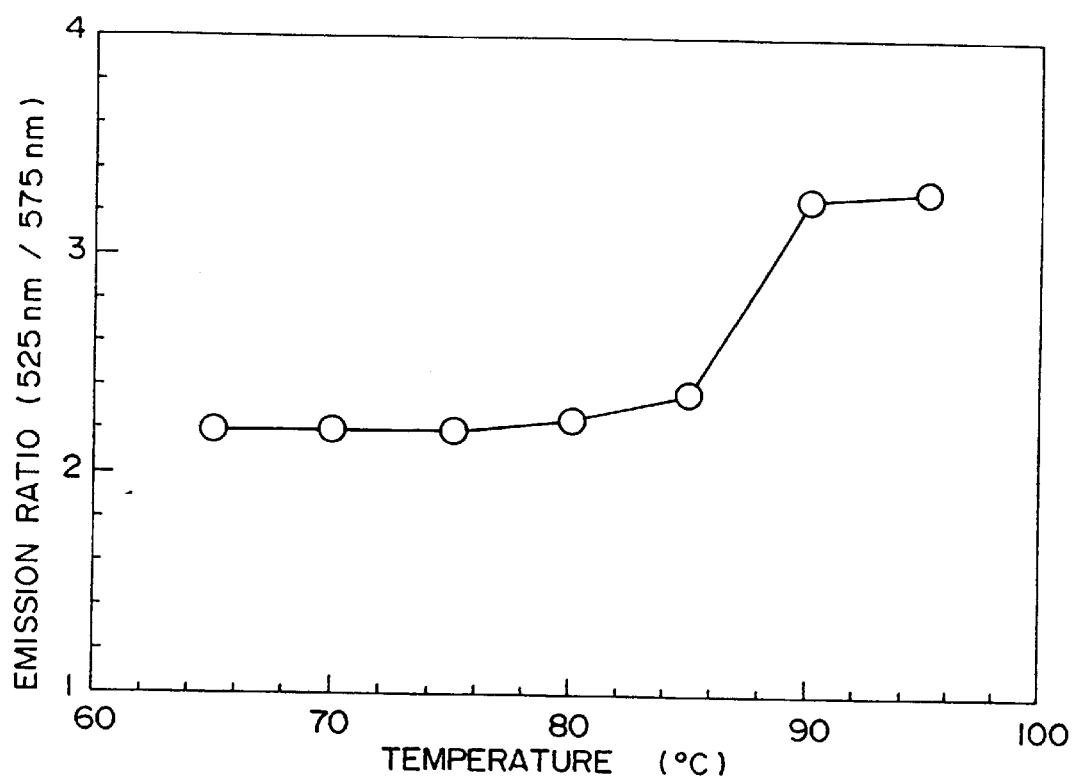
FIG. 14 is a graph showing changes in FRET due to heat denaturation.

When the temperature was raised to 60°–80° C., fluorescein and rhodamine fluorescence was quenched by about 50%, which made it hard to monitor FRET near the melting temperature (see also, Cardullo, C. A., Agawal, S., Flores, C., Zamecnik, P. C., and Wolf, D. E.; (1988) Proc. Natl. Acad. Sci. USA, 85, 8790–8794). Therefore, as described hereinabove, FRET as the ratio of fluorescence emissions was monitored each time after rapidly cooling the samples to 20° C. The monitoring results are shown in FIG. 14. FIG. 14 shows that the melting occurred at about 88° C. as evidenced by the increase of the emission ratio (525/575 nm). In FIG. 14, the stranded-F and stranded-R were mixed in the ratio of 4/5 in 0.15M NaCl and 0.1M Tris-HCl (pH 8.0) and annealed at 65° C. for 30 min. The annealing mixture was heated for 15 min and immediately allowed to cool on ice. The heating temperature was increased in 5° C. increments between 65° and 95° C. (measurements were repeated each time at 20° C.).

As shown in FIG. 14, the emission ratio changed sharply between 85° C. and 90° C., which indicates that denaturation occurred somewhere in this range. This result corresponds with the predicted denaturation temperature (Tm=88.6° C.), which was calculated by the following equation (Meinkoth, J., and Wahl, G.; (1984) Anal. Biochem., 138, 267–284).

$$Tm=81.5° C.+16.6(\log M)+0.41(\% GC)-0.61(\% form) 500/L,$$

wherein M is the molarity of monovalent cations, % GC is the percentage of G and C nucleotides in the DNA, % form is the percentage of formamide in the annealing mixture, and L is the length of the duplex in the base pairs (M=0.15, %GC=56.2, % form=0, and L=224, in the present case).

One way to circumvent this inconvenience of cooling samples each time for measurement is to lower the melting temperature below 60° C. by adding, for instance, a suitable amount of denaturant such as formamide or by lowering the ionic strength. For such a purpose, the FRET was monitored at steady-state between 20° C. and 60° C. at various formamide concentrations (0, 20, 40, and 60%). When the formamide concentration was lower than 40%, the FRET did not change appreciably, while at 60% melting occurred between 40° C. and 60° C.

According to the above equation for Tm, the calculated melting temperature at 60% is 52° C.

Figure 15:
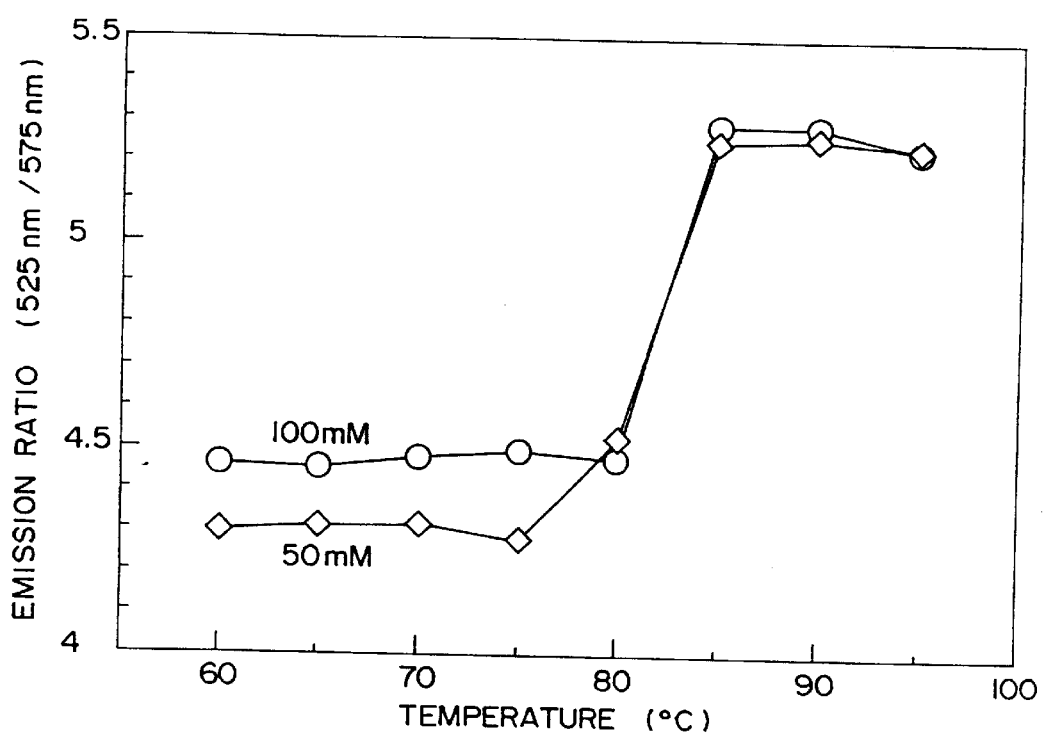
FIG. 15 is a graph showing the effect of salt concentration on heat denaturation.

In the second experiment, the salt concentration, 150 mM in the standard experiments, was lowered to 50 mM or 100 mM. It is known that lower ionic strength lowers the denaturation temperature. The results are shown in FIG. 15. In FIG. 15, the salt concentration, 150 mM in the standard experiment (FIG. 14), was lowered to 50 mM (denoted by "◇") or 100 mM (denoted by "○"). The stranded-F and stranded-R were mixed and annealed at 60° C. for 30 min. The annealing mixture was heated for 15 min and immediately allowed to cool on ice. The heating temperature was increased in 5° C. increments between 65° and 95° C. (measurements were repeated each time at 20° C.).

As shown in FIG. 15, the melting temperature was about 5 to 10 degrees lower in the 50 mM and 100 mM solutions, and the value for the 50 mM solution was somewhat lower than that for the 100 mM solution, again in agreement with the Tm equation as described above.

<FRET in alkali denaturation>

Fluorescein and rhodamine fluorescence is very low in acidic pH and increases on alkalinization, becoming constant at pHs higher than 8. The ratio of emission (525 nm/575 nm) is almost constant at alkaline pH.

Figure 16:
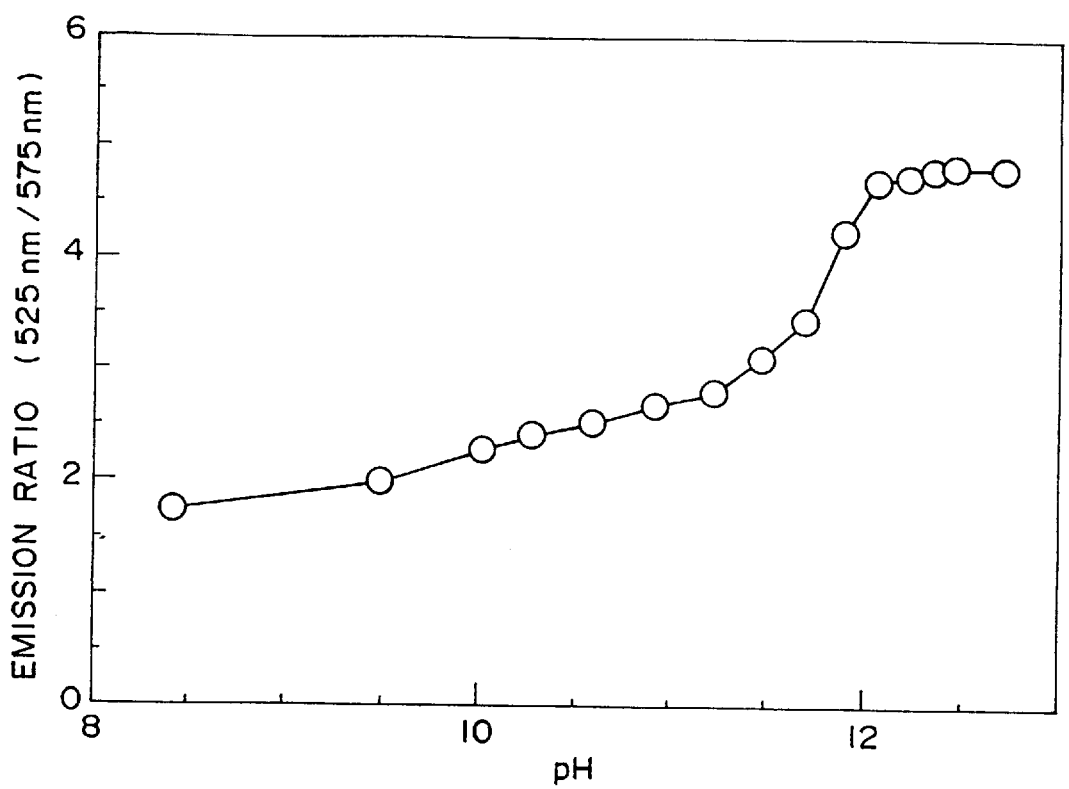
FIG. 16 is a graph showing a fluorescence melting curve for fluorescein-labeled stranded (stranded-F) and rhodamine-labeled stranded (stranded-R) in alkali denaturation.

In this Example, mixtures of the stranded-R and stranded-F were first annealed in glycine buffer (pH 8.3) and the sample pH was raised by adding aliquots of 1N NaOH. The measurement results are shown in FIG. 16. In FIG. 16, the stranded-F and stranded-R were mixed with the ratio of 4/5 in 0.15M NaCl and 0.125M glycine buffer (pH 8.3) and annealed at 65° C. for 30 min. The pH of the annealing mixture was raised by adding aliquots of 1N NaOH (measurements were repeated each time at 20° C.).

As shown in FIG. 16, the emission ratio increased appreciably between pH 11.5 and pH 12, indicating that DNA denaturation could be monitored.

In the Examples described above, DNA denaturation was detected simply and sensitively. More specifically, with complementary but random incorporation of fluorescent labels by PCR, DNA denaturation could be detected with high sensitivity by standard spectrofluorometry.

As described hereinabove, when the apparatus (or method) for detecting denaturation of a nucleic acid according to the first embodiment of the present invention is used, the characteristic fluorescence of a fluorescent molecule provided to a nucleic acid is measured while controlling the denaturation condition at a measurement point in a quasi-static manner, and therefore it is not necessary to conduct electrophoresis in a gel carrier provided with a gradient of denaturation condition. As a result, the denaturation of the nucleic acid can be detected more rapidly with a higher accuracy.

In addition, when the apparatus for detecting denaturation of a nucleic acid according to the second embodiment of the present invention is used, a nucleic acid to be measured is prepared by using a reference nucleic acid sample and a nucleic acid sample to be examined as starting materials, and then fluorescence is measured in the same manner as in the apparatus according to the first embodiment. As a result, measurement can be conducted more effectively in a through or successive mode.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 175730/1993 filed on Jul. 15, 1993 is hereby incorporated by reference.

What is claimed is:

1. An apparatus for detecting denaturation of a nucleic acid, comprising:

i) means for preparing a first double-strandeded nucleic acid and a second double-strandeded nucleic acid, which first double-strandeded nucleic acid includes a first single-strandeded nucleic acid and a second single-strandeded nucleic acid, and which second double-strandeded nucleic acid includes a third single-strandeded nucleic acid and a fourth single-strandeded nucleic acid, ii) first nucleic acid amplifying means, whereby said first double-strandeded nucleic acid is amplified in a first reaction mixture in the presence of a nucleotide labeled with a first label molecule, a first primer which is complementary to said first single-strandeded nucleic acid, and a second primer coupled with a first binding molecule, which is complementary to said second single-strandeded nucleic acid, under conditions appropriate to produce a large number of fifth and sixth single-strandeded nucleic acids labeled with said first label molecule, wherein said fifth single-strandeded nucleic acids are complementary to said first single-strandeded molecule, and wherein said sixth single-strandeded nucleic acids are complementary to said second single-strandeded nucleic acid and which are coupled with said first binding molecule, iii) second nucleic acid amplifying means, whereby said second double-strandeded nucleic acid is amplified in a second reaction mixture in the presence of a nucleotide labeled with a second label molecule, a third primer coupled with a binding molecule which is complementary to said third single-strandeded nucleic acid, and a fourth primer which is complementary to said fourth single-strandeded nucleic acid, under conditions appropriate to produce a large number of seventh and eighth single-strandeded nucleic acids labeled with said second label molecule, wherein said seventh single-strandeded nucleic acids are complementary to said third single-strandeded nucleic acid and which are coupled with said second binding molecule, and wherein said eighth single-strandeded nucleic acids are complementary to said fourth single-strandeded molecule wherein said second double-strandeded nucleic acid is the same or substantially the same as said first double-strandeded nucleic acid and said third single-strandeded nucleic acid is the same or substantially the same as said first single-strandeded nucleic acid, and said fourth single-strandeded nucleic acid is the same or substantially the same as said second single-strandeded nucleic acid, and wherein said first label molecule is an energy acceptor and said second label molecule is an energy donor, and said second label molecule is capable of transferring energy to said first label molecule when said fifth single-strandeded nucleic acid is bound to said eighth single-strandeded nucleic acid but not when said fifth single-strandeded nucleic acid is not bound to said eighth single-strandeded nucleic acid;

iv) first extracting means for extracting said fifth single-strandeded nucleic acid, whereby said first reaction mixture is contacted with a solid phase material onto which is adsorbed a first complexing molecule which specifically binds said first binding molecule, under conditions such that said first binding molecule specifically binds with said first complexing molecule to fix said sixth single-strandeded nucleic acid to said solid phase material, and allows said fifth single-strandeded nucleic acid to be eluted therefrom, v) second extracting means for extracting said eighth single-strandeded nucleic acid, whereby said second reaction mixture is contacted with a solid phase material onto which is adsorbed a second complexing molecule which specifically binds said second binding molecule, under conditions such that said second binding molecule specifically binds with said second complexing molecule to fix said seventh single-strandeded nucleic acid to said solid phase material, and allows said eighth single-strandeded nucleic acid to be eluted therefrom, vi) connecting means for directing said fifth single-strandeded nucleic acid and said eighth single-strandeded nucleic acid into a nucleic acid mixing means;

vii) nucleic acid mixing means, for mixing said fifth single-strandeded nucleic acid and said eighth single-strandeded nucleic acid under such conditions to produce a third double-strandeded nucleic acid comprising said fifth single-strandeded nucleic acid and said eighth single-strandeded nucleic acid;

viii) denaturation condition controlling means for regulating one or more conditions affecting the denaturation of said third double-strandeded nucleic acid, whereby the regulation of said conditions controls and facilitates denaturation;

ix) excitation light irradiation means positioned so as to irradiate said first and second label molecules, for irradiating at least one of said first and second label molecules before regulation of conditions by said denaturation condition controlling means and when said fifth single-strandeded nucleic acid is bound to said eighth single-strandeded nucleic acid, and for irradiating at least one of said first and second label molecules after regulation of conditions by said denaturation condition controlling means and when said fifth single-strandeded nucleic acid is not bound to said eighth single-strandeded nucleic acid;

x) fluorescence detection means for detecting fluorescence emitted by at least one of said first and second label molecules irradiated before and after regulation of conditions by said denaturation condition controlling means;

xi) processing means for receiving, storing, processing and measuring a signal supplied from said fluorescence detection means;

whereby one or more conditions affecting denaturation of said third double-strandeded nucleic acid are regulated by said denaturation condition controlling means in such a manner as to control and facilitate denaturation of said third double-strandeded nucleic acid;

whereby at least one of said first and second label molecules are irradiated by said excitation light irradiation means before and after said regulation of conditions;

whereby fluorescence emitted by at least one of said first and second label molecules irradiated before said regulation of conditions and fluorescence emitted by at least one of said first and second label molecules irradiated after said regulation of conditions is detected by said fluorescence detection means and measured and processed by said processing means, and whereby a difference between fluorescence emitted by at least one of said first and second label molecules irradiated before said regulation of conditions and fluorescence emitted by at least one of said first and second label molecules irradiated after said regulation of conditions is indicative of denaturation of said double-strandeded nucleic acid.

2. An apparatus for detecting denaturation of a nucleic acid according to claim 1, wherein said fluorescence detection means detects a change in fluorescence emission which is caused by a change in the amount of energy transfer between said first label molecule and said second label molecule, whereby a point of denaturation is determined by calculating when said change in the amount of energy transfer occurs.

3. An apparatus for detecting denaturation of a nucleic acid according to claim 1, wherein at least one of the condition regulated by said denaturation condition controlling means is temperature and said denaturation condition controlling means comprises a temperature controller.

4. An apparatus for detecting denaturation of a nucleic acid according to claim 1, wherein at least one of the condition regulated by said denaturation condition controlling means is hydrogen ion concentration and said denaturation condition controlling means comprises a hydrogen ion concentration controller.

5. An apparatus for detecting denaturation of a nucleic acid according to claim 1, wherein at least one of the condition regulated by said denaturation condition controlling means is the concentration of a denaturing agent capable of denaturing the third double-strandeded nucleic acid and the denaturation condition controlling means comprises a denaturing agent concentration controller.

6. An apparatus for detecting denaturation of a nucleic acid according to claim 1, wherein the fluorescence detection means detects a change in fluorescence which is emitted from said first label molecule only, which change is caused by a change in the amount of energy transfer between said first label molecule and said second label molecule, and the processing means calculates when denaturation occurs by calculating when said change in the amount of energy transfer occurs.

7. An apparatus for detecting denaturation of a nucleic acid according to claim 1, wherein the fluorescence detection means detects a chance in fluorescence which is emitted from said second label molecule only, which chance is caused by a change in the amount of energy transfer between said first label molecule and said second label molecule, and the processing means calculates when denaturation occurs by calculating when said change in the amount of energy transfer occurs.

8. An apparatus for detecting denaturation of a nucleic acid according to claim 1, wherein the fluorescence detection means detects a change in the lifetime of fluorescence, which chance is caused by a change in the amount of energy transfer between said first label molecules and said second label molecule, and the processing means calculates when denaturation occurs by calculating when said change in the amount of energy transfer occurs.

9. An apparatus for detecting denaturation of a nucleic acid according to claim 1, wherein the fluorescence detection means detects a change in the wavelength of fluorescence, which chance is caused by a change in the amount of energy transfer between said first label molecule and said second label molecule, and the processing means calculates when denaturation occurs by calculating when said change in the amount of energy transfer occurs.

10. An apparatus for detecting denaturation of a nucleic acid according to claim 9, wherein the fluorescence detection means comprises a fluorescence wavelength measuring device.

11. An apparatus for detecting denaturation of a nucleic acid according to claim 10, wherein the fluorescence detection means comprises a device which measures time-resolved fluorescence.

12. An apparatus for detecting denaturation of a nucleic acid, comprising:
   i) means for preparing a first double-strandeded nucleic acid and a second double-strandeded nucleic acid, which first double-strandeded nucleic acid includes a first single-strandeded nucleic acid and a second single-strandeded nucleic acid, and which second double-strandeded nucleic acid includes a third single-strandeded nucleic acid and a fourth single-strandeded nucleic acid,
   ii) first nucleic acid amplifying means,
   whereby said first double-strandeded nucleic acid is amplified in a first reaction mixture in the presence of a nucleotide labeled with a first label molecule, a first primer which is complementary to said first single-strandeded nucleic acid, and a second primer coupled with a first binding molecule, which is complementary to said second single-strandeded nucleic acid, under conditions appropriate to produce a large number of fifth and sixth single-strandeded nucleic acids labeled with said first label molecule, wherein said fifth single-strandeded nucleic acids are complementary to said first single-strandeded molecule and wherein said sixth single-strandeded nucleic acids are complementary to said second single-strandeded nucleic acid and which are coupled with said first binding molecule,
   iii) second nucleic acid amplifying means,
   whereby said second double-strandeded nucleic acid is amplified in a second reaction mixture in the presence of a nucleotide labeled with a second label molecule, a third primer coupled with a binding molecule which is complementary to said third single-strandeded nucleic acid, and a fourth primer which is complementary to said fourth single-strandeded nucleic acid, under conditions appropriate to produce a large number of seventh and eighth single-strandeded nucleic acids labeled with said second label molecule, wherein said seventh single-strandeded nucleic acids are complementary to said third single-strandeded nucleic acid and which are coupled with said second binding molecule and wherein said eighth single-strandeded nucleic acids are complementary to said fourth single-strandeded molecule
   wherein said second double-strandeded nucleic acid is the same or substantially the same as said first double-strandeded nucleic acid and said third single-strandeded nucleic acid is the same or substantially the same as said first single-strandeded nucleic acid, and said fourth single-strandeded nucleic acid is the same or substantially the same as said second single-strandeded nucleic acid,
   wherein said first label molecule is an energy acceptor and said second label molecule is an energy donor, and said second label molecule is capable of transferring energy to said first label molecule when said fifth single-strandeded nucleic acid is bound to said eighth single-strandeded nucleic acid but not when said fifth single-strandeded nucleic acid is not bound to said eighth single-strandeded nucleic acid;
   iv) first extracting means for extracting said fifth single-strandeded nucleic acid, whereby said first reaction mixture is contacted with a solid phase material onto which is adsorbed a first complexing molecule which specifically binds said first binding molecule, under conditions such that said first binding molecule specifically binds with said first complexing molecule to fix said sixth single-strandeded nucleic acid to said solid phase material, and allows said fifth single-strandeded nucleic acid to be eluted therefrom,
   v) second extracting means for extracting said eighth single-strandeded nucleic acid, whereby said second reaction mixture is contacted with a solid phase material onto which is adsorbed a second complexing molecule which specifically binds said second binding molecule, under conditions such that said second binding molecule specifically binds with said second complexing molecule to fix said seventh single-strandeded nucleic acid to said solid phase material, and allows said eighth single-strandeded nucleic acid to be eluted therefrom,
   vi) connecting means for directing said fifth single-strandeded nucleic acid and said eighth single-strandeded nucleic acid into a nucleic acid mixing means;
   vii) nucleic acid mixing means,
      for mixing said fifth single-strandeded nucleic acid and said eighth single-strandeded nucleic acid under such conditions to produce a third double-strandeded nucleic acid comprising said fifth single-strandeded nucleic acid and said eighth single-strandeded nucleic acid;
   viii) denaturation condition controlling means for regulating one or more conditions affecting the denaturation of said third double-strandeded nucleic acid, whereby the regulation of said conditions controls and facilitates denaturation;
   whereby said nucleic acid mixing means and said denaturation condition controlling means are positioned in the same container in said apparatus;
   ix) excitation light irradiation means positioned so as to irradiate said first and second label molecules, for irradiating at least one of said first and second label molecules before regulation of conditions by said denaturation condition controlling means and when said fifth single-strandeded nucleic acid is bound to said eighth single-strandeded nucleic acid, and for irradiating at least one of said first and second label molecules after regulation of conditions by said denaturation condition controlling means and when said fifth single-strandeded nucleic acid is not bound to said eighth single-strandeded nucleic acid;

x) fluorescence detection means for detecting fluorescence emitted by at least one of said first and second label molecules irradiated before and after regulation of conditions by said denaturation condition controlling means;

xi) processing means for receiving, storing, processing and measuring a signal supplied from said fluorescence detection means;

whereby one or more conditions affecting denaturation of said third double-strandeded nucleic acid are regulated by said denaturation condition controlling means in such a manner as to control and facilitate denaturation of said third double-strandeded nucleic acid;

whereby at least one of said first and second label molecules are irradiated by said excitation light irradiation means before and after said regulation of conditions;

whereby fluorescence emitted by at least one of said first and second label molecules irradiated before said regulation of conditions and fluorescence emitted by at least one of said first and second label molecules irradiated after said regulation of conditions is detected by said fluorescence detection means and measured and processed by said processing means, and whereby a difference between fluorescence emitted by at least one of said first and second label molecules irradiated before said regulation of conditions and fluorescence emitted by at least one of said first and second label molecules irradiated after said regulation of conditions is indicative of denaturation of said double-strandeded nucleic acid.

* * * * *